United States Patent
Anderson et al.

(10) Patent No.: US 6,955,916 B2
(45) Date of Patent: *Oct. 18, 2005

(54) PROTEINASE INHIBITOR, PRECURSOR THEREOF AND GENETIC SEQUENCES ENCODING SAME

(75) Inventors: Marilyn Anne Anderson, Keilor (AU); Angela Hilary Atkinson, Montrose (AU); Robyn Louise Heath, Williamstown (AU); Adrienne Elizabeth Clarke, Parkville (AU)

(73) Assignee: Hexima Limited, Melbourne (AU)

( * ) Notice: Subject to any disclaimer, the term of this patent is extended or adjusted under 35 U.S.C. 154(b) by 219 days.

This patent is subject to a terminal disclaimer.

(21) Appl. No.: 10/164,961

(22) Filed: Jun. 7, 2002

(65) Prior Publication Data

US 2003/0096388 A1 May 22, 2003

Related U.S. Application Data

(60) Continuation of application No. 09/431,498, filed on Nov. 1, 1999, now Pat. No. 6,440,727, which is a division of application No. 08/454,295, filed as application No. PCT/AU93/00659 on Dec. 16, 1993, now Pat. No. 6,031,087.

(30) Foreign Application Priority Data

Dec. 16, 1992 (AU) .............................................. PL6399

(51) Int. Cl.[7] .......................... C12N 15/00; C12N 9/76; C12N 9/50; C07H 21/04
(52) U.S. Cl. .................... 435/320.1; 435/213; 435/219; 435/252.3; 536/23.2
(58) Field of Search ............................... 435/320.1, 213, 435/219, 252.3; 536/23.2, 23.6; 800/278, 295

(56) References Cited

U.S. PATENT DOCUMENTS 6,031,087 A * 2/2000 Anderson et al. .......... 536/23.2
6,440,727 B1 * 8/2002 Anderson et al. ........ 435/320.1

OTHER PUBLICATIONS

Bryant, et al. (1976) "Proteinase Inhibitor II from Potatoes: Isolation and Characterization of its Protomer Components": *Biochemistry* 15(16): 3418–3423.

Choi, et al (1990) "Primary structure of two Proteinase Inhibitor genes closely linked in the Potato genome": *Hanguk Saenghwahakhoe Chi* 23: 214–220.

Suggs, et al. (1981) "Use of synthetic oligonucleotides as hybridization probes: Isolation of cloned cDNA sequences for human $\beta_2$–microglobulin": *Proc. Nat'l. Acad. Sci. USA* 78(11):6613–6617.

* cited by examiner

*Primary Examiner*—Tekchand Saidha
(74) *Attorney, Agent, or Firm*—Scully, Scott, Murphy & Presser

(57) ABSTRACT

The present invention relates generally to proteinase inhibitors, a precursor thereof and to genetic sequences encoding same. More particularly, the present invention relates to a nucleic acid molecule comprising a sequence of nucleotides which encodes or is complementary to a sequence which encodes a type II serine proteinase inhibitor (PI) precursor from a plant wherein the precursor comprises at least three PI monomers and wherein at least one of the monomers has a chymotrypsin specific site and at least one other of the monomers has a trypsin specific site.

9 Claims, 21 Drawing Sheets

Figure 2:
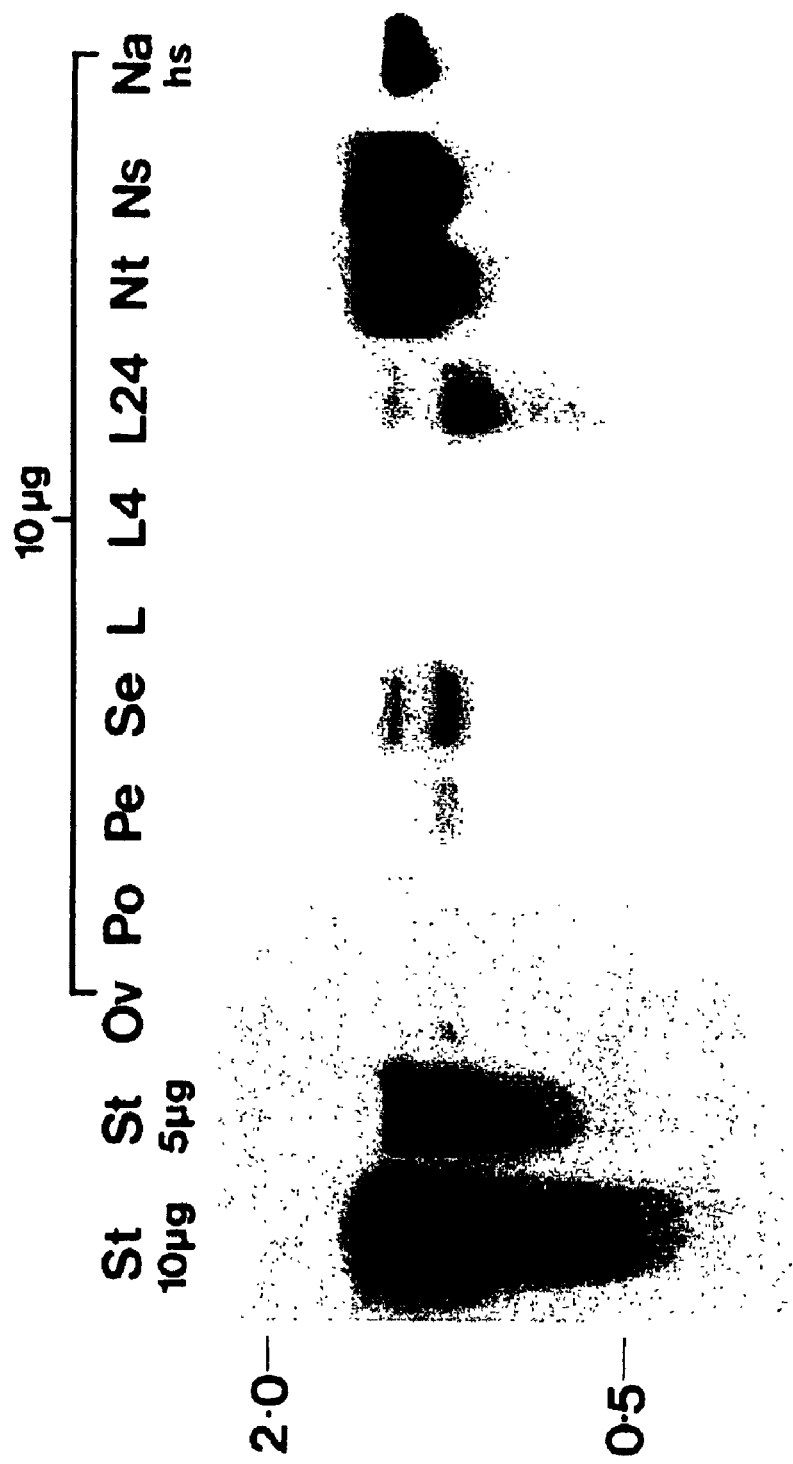

```
CAC AGA GTT AGT TTC CTT GCT CTC CTC TTA TTT GGA ATG TCT CTG        18
His Arg Val Ser Phe Leu Ala Leu Leu Leu Phe Gly Met Ser Leu
            -20

CGA GTA AGT ATG GCT GTT                                            66
Arg Val Ser Met Ala Val
        -29

CTT GTA AGC AAT GTG GAA CAT GCA GAT GCC AAG GCT TGT ACC TTA AAC   114
Leu Val Ser Asn Val Glu His Ala Asp Ala Lys Ala Cys Thr Leu Asn
-10                                     -1  1                 5

TGT GAT CCA AGA ATT GCC TAT GGA GTT TGC CCG CGT TCA GAA AAG       162
Cys Asp Pro Arg Ile Ala Tyr Gly Val Cys Pro Arg Ser Glu Lys
            10                      15                  20

AAG AAT GAT CGG ATA TGC ACC AAC TGT TGC GCA GGC ACG AAG GGT TGT   210
Lys Asn Asp Arg Ile Cys Thr Asn Cys Cys Ala Gly Thr Lys Gly Cys
        25                  30                  35

AAG TAC TTC AGT GAT GAT GGA ACT TTT GTT TGT GAA GGA GAG TCT GAT   258
Lys Tyr Phe Ser Asp Asp Gly Thr Phe Val Cys Glu Gly Glu Ser Asp
        40                  45                  50
```

Figure 1a

```
CCT AGA AAT CCA AAG GCT TGT ACC TTA AAC TGT GAT CCA AGA ATT GCC    306
Pro Arg Asn Pro Lys Ala Cys Thr Leu Asn Cys Asp Pro Arg Ile Ala
 55                  60                  65                  70

TAT GGA GTT TGC CCG CGT TCA GAA GAA AAG AAG AAT GAT CGG ATA TGC    354
Tyr Gly Val Cys Pro Arg Ser Glu Glu Lys Lys Asn Asp Arg Ile Cys
             75                  80                  85

ACC AAC TGT TGC GCA GGC ACG AAG GGT TGT AAG TAC TTC AGT GAT GAT    402
Thr Asn Cys Cys Ala Gly Thr Lys Gly Cys Lys Tyr Phe Ser Asp Asp
         90                  95                 100

GGA ACT TTT GTT TGT GAA GGA GAG TCT GAT CCT AGA AAT CCA AAG GCT    450
Gly Thr Phe Val Cys Glu Gly Glu Ser Asp Pro Arg Asn Pro Lys Ala
     105                 110                 115

TGT CCT CGG AAT TGC GAT CCA GAT CGG ATT GCC TAT GGG ATT TGC CCA CTT    498
Cys Pro Arg Asn Cys Asp Pro Asp Arg Ile Ala Tyr Gly Ile Cys Pro Leu
 120                 125                 130

GCA GAA AAG AAG AAT GAT CGG ATA TGC ACC AAC TGT TGC GCA GGC    546
Ala Glu Lys Lys Asn Asp Arg Ile Cys Thr Asn Cys Cys Ala Gly
 135                 140                 145                 150
```

Figure 1b

```
AAA AAG GGT TGT AAG TAC TTT AGT GAT GAT GGA ACT TTT GTT TGT GAA    594
Lys Lys Gly Cys Lys Tyr Phe Ser Asp Asp Gly Thr Phe Val Cys Glu
            155                 160                 165

GGA GAG TCT GAT CCT AAA AAT CCA AAG GCC TGT CCT CGG AAT TGT GAT    642
Gly Glu Ser Asp Pro Lys Asn Pro Lys Ala Cys Pro Arg Asn Cys Asp
        170                 175                 180

GGA AGA ATT GCC TAT GGG ATT TGC CCA CTT TCA GAA GAA AAG AAT        690
Gly Arg Ile Ala Tyr Gly Ile Cys Pro Leu Ser Glu Glu Lys Asn
            185                 190                 195

GAT CGG ATA TGC ACC AAC TGC TGC GCA GGC AAA AAG GGT TGT AAG TAC    738
Asp Arg Ile Cys Thr Asn Cys Cys Ala Gly Lys Lys Gly Cys Lys Tyr
        200                 205                 210

TTT AGT GAT GAT GGA ACT TTT GTT TGT GAA GGA GAG TCT GAT CCT AAA    786
Phe Ser Asp Asp Gly Thr Phe Val Cys Glu Gly Glu Ser Asp Pro Lys
            215                 220                 225         230

AAT CCA AAG GCT TGT CCT CGG AAT TGT GAT GGA AGA ATT GCC TAT GGG    834
Asn Pro Lys Ala Cys Pro Arg Asn Cys Asp Gly Arg Ile Ala Tyr Gly
        235                 240                 245
```

Figure 1c

```
ATT TGC CCA CTT TCA GAA GAA AAG AAT GAT CGG ATA TGC ACA AAC      882
Ile Cys Pro Leu Ser Glu Glu Lys Asn Asp Arg Ile Cys Thr Asn
    250                     255                     260

TGT TGC GCA GGC AAA AAG GGC TGT AAG TAC TTT AGT GAT GAT GGA ACT  930
Cys Cys Ala Gly Lys Lys Gly Cys Lys Tyr Phe Ser Asp Asp Gly Thr
        265                     270                     275

TTT GTT TGT GAA GGA GAG TCT GAT CCT AGA AAT CCA AAG GCC TGT CCT  978
Phe Val Cys Glu Gly Glu Ser Asp Pro Arg Asn Pro Lys Ala Cys Pro
    280                     285                     290

CGG AAT TGT GAT GGA AGA ATT GCC TAT GGA ATT TGC CCA CTT TCA GAA 1026
Arg Asn Cys Asp Gly Arg Ile Ala Tyr Gly Ile Cys Pro Leu Ser Glu
        295                     300                     305                 310

GAA AAG AAT GAT CGG ATA TGC ACC AAT TGT TGC GCA GGC AAG AAG     1074
Glu Lys Asn Asp Arg Ile Cys Thr Asn Cys Cys Ala Gly Lys Lys
            315                     320                     325

GGC TGT AAG TAC TTT AGT GAT GAT GGA ACT TTT ATT TGT GAA GGA GAA 1122
Gly Cys Lys Tyr Phe Ser Asp Asp Gly Thr Phe Ile Cys Glu Gly Glu
        330                     335                     340
```

Figure 1d

```
TCT GAA TAT GCC AGC AAA GTG GAT GAA TAT GTT GGT GAA GTG GAG AAT    1170
Aer Glu Tyr Ala Ser Lys Val Asp Glu Tyr Val Gly Glu Val Glu Asn
        345                 350                 355

GAT CTC CAG AAG TCT AAG GTT GCT GTT TCC TAAGTCCTAA CTAATAATAT      1220
Asp Leu Gln Lys Ser Lys Val Ala Val Ser
        360                 365

GTAGTCTATG TATGAAACAA AGGCATGCCA ATATGCTCTG TCTTGCCTGT AATCTGTAAT  1280

ATGGTAGTGG AGCTTTTCCA CTGCCTGTTT AATAAGAAAT GGAGCACTAG TTTGTTTTAG  1340

TTAAAAAAAA AAAAAAAAAA                                              1360
```

Figure 1e

C1  DRICTNCCAGTKGCKYFSDDGTFVCEGESDPRNPKACTLNCDPRIAYGVCPRS
T1  DRICTNCCAGTKGCKYFSDDGTFVCEGESDPRNPKACPRNCDPRIAYGICPL
T2  DRICTNCCAGKKGCKYFSDDGTFVCEGESDPKNPKACPRNCDGRIAYGICPLS
T3  DRICTNCCAGKKGCKYFSDDGTFVCEGESDPKNPKACPRNCDGRIAYGICPLS
T4  DRICTNCCAGKKGCKYFSDDGTFVCEGESDPRNPKACPRNCDGRIAYGICPLS
    1         10        20        30        40        50

PROTEINASE INHIBITOR, PRECURSOR THEREOF AND GENETIC SEQUENCES ENCODING SAME

CROSS REFERENCE TO RELATED APPLICATIONS

The present application is a continuation of Ser. No. 09/431,498, filed Nov. 1, 1999 now U.S. Pat. No. 6,440,727, which is a divisional of Ser. No. 08/454,295, filed Sep. 1, 1995 now U.S. Pat. No. 6,031,089, which corresponds to PCT/AU93/00659 having an international filing date of Dec. 16, 1993.

The present invention relates generally to proteinase inhibitors, a precursor thereof and to genetic sequences encoding same.

Nucleotide and amino acid sequences are referred to herein by sequence identity numbers (SEQ ID NOs) which are defined after the bibliography. A general summary of the SEQ ID NOs is provided before the examples.

Throughout this specification and the claims which follow, unless the context requires otherwise, the word "comprise", or variations such as "comprises" or "comprising", will be understood to imply the inclusion of a stated element or integer or group of elements or integers but not the exclusion of any other element or integer or group of elements or integers.

Several members of the families Solanaceae and Fabaceae accumulate serine proteinase inhibitors in their storage organs and in leaves in response to wounding (Brown and Ryan, 1984; Richardson, 1977). The inhibitory activities of these proteins are directed against a wide range of proteinases of microbial and animal origin, but rarely against plant proteinases (Richardson, 1977). It is believed that these inhibitors are involved in protection of the plants against pathogens and predators. In potato tubers and legume seeds, the inhibitors can comprise 10% or more of the stored proteins (Richardson, 1977), while in leaves of tomato and potato (Green and Ryan, 1972), and alfalfa (Brown and Ryan, 1984), proteinase inhibitors can accumulate to levels of 2% of the soluble protein within 48 hours of insect attack, or other types of wounding (Brown & Ryan, 1984; Graham et al, 1986). High levels of these inhibitors (up to 50% of total soluble protein) are also present in unripe fruits of the wild tomato, *Lycopersicon peruvianum* (Pearce et al., 1988).

There are two families of serine proteinase inhibitors in tomato and potato (Ryan, 1984). Type I inhibitors are small proteins (monomer Mr 8100) which inhibit chymotrypsin at a single reactive site (Melville and Ryan, 1970; Plunkett et al., 1982). Inhibitors of the type II family generally contain two reactive sites, one of which inhibits chymotrypsin and the other trypsin (Bryant et al., 1976; Plunkett et. al., 1982). The type II inhibitors have a monomer Mr of 12,300 (Plunkett et al., 1982). Proteinase inhibitor I accumulates in etiolated tobacco (*Nicoliana tabacum*) leaves (Kuo et al., 1984), and elicitors from *Phytophthora parasitica* var. *nicotianae* were found to induce proteinase inhibitor I accumulation in tobacco cell suspension cultures (Rickauer et al., 1989).

There is a need to identify other proteinase inhibitors and to investigate their potential use in the development of transgenic plants with enhanced protection against pathogens and predators. In accordance with the present invention, genetic sequences encoding a proteinase inhibitor precursor have been cloned. The precursor has multi-proteinase inhibitor domains and will be useful in developing a range of transgenic plants with enhanced proteinase inhibitor expression. Such plants will have enhanced protective properties against pathogens and predators. The genetic constructs of the present invention will also be useful in developing vaccines for ingestion by insects which are themselves predators or which act as hosts for plant pathogens. The recombinant precursor or monomeric inhibitors will also be useful in topical sprays and in assisting animals in feed digestion.

Accordingly, one aspect of the present invention relates to a nucleic acid molecule comprising a sequence of nucleotides which encodes or is complementary to a sequence which encodes a type II serine proteinase inhibitor (PI) precursor from a plant wherein said precursor comprises at least three PI monomers and wherein at least one of said monomers has a chymotrypsin specific site and at least one other of said monomers has a trypsin specific site.

The "nucleic acid molecule" of the present invention may be RNA or DNA (eg cDNA), single or double stranded and linear or covalently closed. The nucleic acid molecule may also be genomic DNA corresponding to the entire gene or a substantial portion thereof or to fragments or derivatives thereof. The nucleotide sequence may correspond to the naturally occurring nucleotide sequence of the genomic or cDNA clone or may contain single or multiple nucleotide substitutions, deletions and/or additions thereto. All such variants in the nucleic acid molecule either retain the ability to encode at least one monomer or active part thereof or are useful as hybridisation probes or polymerase chain reaction (PCR) primers for the same or similar genetic sequences in other sources.

Preferably, the PI precursor comprises at least four, more preferably at least five and even more preferably at least six PI monomers. Still more preferably, the PI precursor further comprises a signal sequence. The PI precursor of the present invention preferably comprises amino acid sequences which are process sites for cleavage into individual monomers.

The term "precursor" as used herein is not intended to place any limitation on the utility of the precursor molecule itself or a requirement that the molecule first be processed into monomers before PI activity is expressed. The precursor molecule has PI activity and the present invention is directed to the precursor and to the individual monomers of the precursor.

Furthermore, the present invention extends to a nucleic acid molecule comprising a sequence of nucleotides which encodes or is complementary to a sequence which encodes a hybrid type II serine PI precursor wherein said precursor comprises at least two monomers from different PIs. The at least two monomers may be modified such as being unable to be processed into individual monomers or may retain the ability to be so processed. Preferably, at least one of said monomers has a chymotrypsin specific site and the other of said monomers has a trypsin specific site. Preferably there are at least three monomers, more preferably at least four monomers, still more preferably at least five monomers and yet still more preferably at least six monomers wherein at least two are from different PIs. In a most preferred embodiment, at least one of said monomers is a thionin. Such hybrid PI precursors and/or monomers thereof are particularly useful in generating molecules which are "multi-valent" in that they are active against a range of pathogens and predators such as both fungi and insects. Accordingly, reference herein to "PI precursor" includes reference to hybrid molecules.

The present invention is exemplified by the isolation of the subject nucleic acid molecule from *Nicotiana alata* which has the following nucleotide sequence (SEQ ID NO. 1) and a corresponding amino acid sequence (SEQ ID NO. 3):

"equivalent" and "substantially similar" is meant at the level of nucleotide sequence, amino acid sequence, antibody reactivity, monomer composition and/or processing of the

```
                                        AAG GCT TGT ACC TTA AAC
                                        Lys Ala Cys Thr Leu Asn

TGT GAT CCA AGA ATT GCC TAT GGA GTT TGC CCG CGT TCA GAA GAA AAG
Cys Asp Pro Arg Ile Ala Tyr Gly Val Cys Pro Arg Ser Glu Glu Lys

AAG AAT GAT CGG ATA TGC ACC AAC TGT TGC GCA GGC ACG AAG GGT TGT
Lys Asn Asp Arg Ile Cys Thr Asn Cys Cys Ala Gly Thr Lys Gly Cys

AAG TAG TTC AGT GAT GAT GGA ACT TTT GTT TGT GAA GGA GAG TCT GAT
Lys Tyr Phe Ser Asp Asp Gly Thr Phe Val Cys Glu Gly Glu Ser Asp

CCT AGA AAT CCA AAG GCT TGT ACC TTA AAC TGT GAT CCA AGA ATT GCC
Pro Arg Asn Pro Lys Ala Cys Thr Leu Asn Cys Asp Pro Arg Ile Ala

TAT GGA GTT TGC CCG CGT TGA GAA GAA AAG AAG AAT GAT CGG ATA TGC
Tyr Gly Val Cys Pro Arg Ser Glu Glu Lys Lys Asn Asp Arg Ile Cys

ACC AAC TGT TGC GCA GGC ACG AAG GGT TGT AAG TAC TTC AGT GAT GAT
Thr Asn Cys Cys Ala Gly Thr Lys Gly Gys Lys Tyr Phe Ser Asp Asp

GGA ACT TTT GTT TGT GAA GGA GAG TCT GAT CCT AGA AAT CCA AAG GCT
Gly Thr Phe Val Cys Glu Gly Glu Ser Asp Pro Arg Asn Pro Lys Ala

TGT CCT CGG AAT TGC GAT CCA AGA ATT GCC TAT GGG ATT TGC CCA CTT
Cys Pro Arg Asn Cys Asp Pro Arg Ile Ala Tyr Gly Ile Cys Pro Leu

CCA CAA CAA AAC AAC AAT CAT CGG ATA TGC ACC AAC TCT TGC GCA GGC
Ala Glu Glu Lys Lys Asn Asp Arg Ile Cys Thr Asn Cys Cys Ala Gly

AAA AAG CGT TGT AAG TAC TTT AGT GAT GAT GGA ACT TTT GTT TGT GAA
Lys Lys Gly Cys Lys Tyr Phe Ser Asp Asp Gly Thr Phe Val Cys Glu

GGA GAG TCT GAT CCT AAA AAT CCA AAG GCC TGT CCT CGG AAT TGT GAT
Gly Glu Ser Asp Pro Lys Asn Pro Lys Ala Cys Pro Arg Asn Cys Asp

GGA AGA ATT GCC TAT GGG ATT TGC CCA CTT TCA GAA GAA AAG AAG AAT
Gly Arg Ile Ala Tyr Gly Ile Cys Pro Leu Ser Glu Glu Lys Lys Asn

GAT CGG ATA TGC ACC AAC TGC TGC GCA GGC AAA AAG GGT TGT AAG TAC
Asp Arg Ile Cys Thr Asn Cys Cys Ala Gly Lys Lys Gly Cys Lys Tyr

TTT ACT CAT CAT GGA ACT TTT GTT TGT CAA GGA GAG TCT GAT CCT AAA
Phe Ser Asp Asp Gly Thr Phe Val Cys Glu Gly Glu Ser Asp Pro Lys

AAT CCA AAG GCT TGT CCT CGG AAT TGT GAT GGA AGA ATT GCC TAT GGG
Asn Pro Lys Ala Cys Pro Arg Asn Gys Asp Cly Arg Ile Ala Tyr Cly

ATT TGC CCA CTT TCA GAA GAA AAG AAG AAT GAT CGG ATA TGC ACA AAC
Ile Cys Pro Leu Ser Glu Glu Lys Lys Asn Asp Arg Ile Cys Thr Asn

TGT TGC GCA GGC AAA AAG GGC TGT AAG TAC TTT AGT GAT GAT GGA ACT
Cys Cys Ala Gly Lys Lys Gly Cys Lys Tyr Phe Ser Asp Asp Gly Thr

TTT GTT TGT GAA GGA GAG TCT GAT CCT AGA AAT CCA AAG GCC TGT CCT
Phe Val Cys Glu Gly Glu Ser Asp Pro Arg Asn Pro Lys Ala Cys Pro

CGG AAT TGT GAT GGA AGA ATT GCC TAT GGA ATT TGC CCA CTT TCA GAA
Arg Asn Cys Asp Gly Arg Ile Ala Tyr Gly Ile Cys Pro Leu Ser Glu

GAA AAG AAG AAT GAT CGG ATA TGC ACC AAT TGT TGC GCA GGC AAG AAG
Clu Lys Lys Asn Asp Arg Ile Cys Thr Asn Cys Cys Ala Cly Lys Lys

GGC TGT AAG TAC TTT ACT GAT GAT GGA ACT TTT ATT TGT GAA GGA GAA
Gly Cys Lys Tyr Phe Ser Asp Asp Gly Thr Phe Ile Cys Glu Gly Glu

TCT CAA TAT GCC AGC AAA CTG GAT CAA TAT GTT GGT GAA GTG GAG AAT
Ser Glu Tyr Ala Ser Lys Val Asp Glu Tyr Val Gly Glu Val Glu Asn

GAT CTC CAG AAG TCT AAG GTT GCT GTT TCC
Asp Leu Gln Lys Ser Lys Val Ala Val Ser
```

This is done, however, with the understanding that the present invention extends to an equivalent or substant 90% when compared to the sequence of SEQ ID NO. 1 would be considered "substantially similar" to the subject nucleic acid molecule provided that such a substantially similar sequence encodes a PI precursor having at least three monomers and preferably four, five or six monomers as hereinbefore described.

In a particularly preferred embodiment, the nucleic acid molecule further encodes a signal sequence 5' to the open reading frame and/or a nucleotide sequence 3' of the coding region providing a full nucleotide sequence as follows (SEQ ID NO. 2):

```
CGAGTAAGTA TGGCTGTTCA CAGAGTTAGT TTCCTTGCTC TCCTCCTCTT ATTTGGAATG

TCTCTGCTTG TAAGCAATGT GGAACATGCA GATGCC AAG GCT TGT ACC TTA AAC
                                        Lys Ala Cys Thr Leu Asn

TGT GAT CCA AGA ATT GCC TAT GGA GTT TGC CCG CGT TCA GAA GAA AAG
Cys Asp Pro Arg Ile Ala Tyr Gly Val Cys Pro Arg Ser Glu Glu Lys

AAG AAT GAT CGG ATA TGC ACC AAC TGT TGC GCA GGC ACG AAG GGT TGT
Lys Asn Asp Arg Ile Cys Thr Asn Cys Cys Ala Gly Thr Lys Gly Cys

AAG TAC TTC AGT GAT GAT GGA ACT TTT GTT TGT GAA GGA GAG TCT GAT
Lys Tyr Phe Ser Asp Asp Gly Thr Phe Val Cys Glu Gly Glu Ser Asp

CCT AGA AAT CCA AAG GCT TGT ACC TTA AAC TGT GAT CCA AGA ATT GCC
Pro Arg Asn Pro Lys Ala Cys Thr Leu Asn Cys Asp Pro Arg Ile Ala

TAT GGA GTT TGC CCG CGT TCA GAA GAA AAG AAG AAT GAT CGG ATA TGC
Tyr Gly Val Cys Pro Arg Ser Glu Glu Lys Lys Asn Asp Arg Ile Cys

ACC AAC TGT TGC GCA GGC ACG AAG GGT TGT AAG TAC TTC AGT GAT GAT
Thr Asn Gys Gys Ala Gly Thr Lys Gly Cys Lys T

-continued

```
GAT CTC CAG AAG TCT AAG GTT GCT GTT TCC TAAGTCCTAA CTAATAATAT
Asp Leu Gln Lys Ser Lys Val Ala Val Ser

CTAGTCTATG TATGAAACAA AGGCATGCCA ATATGCTOTG TCTTGCCTGT AATCTGTAAT

ATGGTAGTGG AGCTTTTCCA CTGCCTGTTT AATAAGAAAT GGAGCACTAG TTTGTTTTAG

TTAAAAAAAA AAAAAAAAAA
``` including substantially similar variants thereof.

Accordingly, a preferred embodiment of the present invention provides a nucleic acid molecule comprising a sequence of nucleotides as set forth in SEQ ID NO. 1 or 2 which encodes or is complementary to a sequence which encodes a type II serine PI precursor from *Nicotiana alata* or having at least 55% similarity to said precursor or at least one domain therein wherein said precursor comprises a signal peptide and at least five monomers and wherein one of said monomers has a chymotrypsin specific site and four of said monomers have trypsin specific sites.

In still a more preferred embodiment, the nucleic acid molecule is a cDNA molecule and comprises a nucleotide sequence generally as set forth in SEQ ID NO. 1 or 2 or being substantially similar thereto as hereinbefore defined to the whole of said sequence or to a domain thereof.

Another aspect of the present invention is directed to a nucleic acid molecule comprising a sequence of nucleotides which encodes or is complementary to a sequence which encodes a single type II serine PI having either a chymotrypsin specific site or a trypsin specific site and wherein said PI is a monomer of a precursor PI having at least three monomers of which at least one of said monomers has a chymotrypsin site and the other of said monomers has a trypsin site. Preferably, however, the precursor has four, five or six monomers and is as hereinbefore defined.

In its most preferred embodiment, the plant is *N. alata* (Link et Otto) having self-incompatibility genotype $S_1S_3$, $S_3S_3$ or $S_6S_6$, and the nucleic acid molecule is isolatable from or complementary to genetic sequences isolatable from stigmas and styles of mature plants. The corresponding mRNA is approximately 1.4 kb and the cDNA has six conserved domains wherein the first two domains are 100% identical and contain chymotrypsin-specific sites (Leu-Asn). The third, fourth and fifth domains share 95–98% identity and have sites specific for tpypsin (Arg-Asn). A sixth domain which also has a trypsin specific site has less identity to the third, fourth and fifth domains (79–90%) due mainly to a divergent 3' sequence (see Table 1). The preferred PI inhibitor of the present invention has a molecular weight of approximately 42–45 kDa with an approximately 29 amino acid signal sequence.

The N-terminal sequence of the monomeric PI is represented in each of the six repeated domains in the predicted sequence of the PI precursor protein. Thus, it is likely that the PI precursor protein is cleaved at six sites to produce seven peptides. Six of the seven peptides, peptides 2, 3, 4, 5, 6 and 7 (FIG. 1, residues 25–82 [SEQ ID NO. 5], 83–140 [SEQ ID NO. 6], 141–198 [SEQ ID NO. 7], 199–256 [SEQ ID NO. 8], 257–314 [SEQ ID NO. 9] and 315–368 [SEQ ID NO. 9], respectively), would be in the same molecular weight range as the monomeric PI (about 6 kDa) and would have the same N-terminal sequence. Peptide 7 does not contain a consensus site for trypsin or chymotrypsin. Peptide 1 (residues 1–24 [SEQ ID NO. 4], FIG. 1) is smaller than 6 kD, has a different N-terminus and was not detected in a purified monomeric PI preparation. It could be envisaged that peptide 1 and peptide 7 would form a functional proteinase inhibitor with the inhibitory site on peptide 1 held in the correct conformation by disulphide bonds formed between the two peptides.

Although not intending to limit the present invention to any one hypothesis, the PI precursor may be processed by a protease responsible, for example, for cleavage of an Asn-Asp linkage, to produce the bioactive monomers. More particularly, the protease sensitive sequence is $R_1$-$X_1$-$X_2$-Asn-Asp-$R_2$ where $R_1$, $R_2$, $X_1$ and $X_2$ are defined below. The discovery of such a sequence will enable the engineering of peptides and polypeptides capable of being processed in a plant by cleavage of the protease sensitive sequence. According to this aspect of the present invention there is provided a protease sensitive peptide comprising the amino acid sequence:

$$-X_1-X_2-Asn-Asp-$$

wherein $X_1$ and $X_2$ are any amino acid but are preferably both Lys residues. The protease sensitive peptide may also be represented as:

$$R_1-X_1-X_2-Asn-Asp-R_2$$

wherein $X_1$ and $X_2$ are preferably the same and are preferably both Lys residues and wherein $R_1$ and $R_2$ are the same or different, any D or L amino acid, a peptide, a polypeptide, a protein, or a non-amino acid moiety or molecule such as, but not limited to, an alkyl (eg methyl, ethyl), substituted alkyl, alkenyl, substituted alkenyl, acyl, dienyl, arylalkyl, arylalkenyl, aryl, substituted aryl, heterocyclic, substituted heterocyclic, cycloalkyl, substituted cycloalkyl, halo (e.g. Cl, Br, I, F), haloalkyl, nitro, hydroxy, thiol, sulfonyl, carboxy, alkoxy, aryloxy and alkylaryloxy group and the like as would be apparent to one skilled in the art. By alkyl, substitued alkyl, alkenyl and substituted alkenyl and the like is meant to encompass straight and branched molecules, lower ($C_1$–$C_6$) and higher (more than $C_6$) derivatives. The term "substituted" includes all the substituents set forth above.

In its most preferred embodiment, the protease sensitive peptide is:

$$R_1-X_1-X_2-Asn-Asp-R_2$$

wherein $R_1$ and $R_2$ are the same or different and are peptides or polypeptides and wherein $X_1$ and $X_2$ are both Lys residues.

Such a protease sensitive peptide can be placed between the same or different monomers so that upon expression in a suitable host or in vitro, the larger molecule can be processed to the peptides located between the protease sensitive peptides.

The present invention also extends to a nucleic acid molecule comprising a sequence of nucleotides which encodes or is complementary to a sequence which encodes a protease sensitive peptide comprising the sequence:

$$-X_1-X_2-Asn-Asp-$$

wherein $X_1$ and $X_2$ are preferably the same and are most preferably both Lys residues. Such a nucleic acid molecule may be part of a larger nucleotide sequence encoding, for example, a precursor polypeptide capable of being processed via the protease sensitive sequence into individual peptides or monomers.

The protease sensitive peptide of the present invention is particularly useful in generating poly and/or multi-valent "precursors" wherein each monomer is the same or different and directed to the same or different activities such as anti-viral, anti-bacterial, anti-fungal, anti-pathogen and/or anti-predator activity.

Although not wishing to limit this aspect of the invention to any one hypothesis or proposed mechanism of action, it is believed that the protease acts adjacent the Asn residue as more particularly between the Asn-Asp residues.

The present invention extends to an isolated type II serine PI precursor from a plant wherein said precursor comprises at least three PI monomers and wherein at least one of said monomers has a chymotrypsin specific site and at least one other of said monomers has a trypsin specific site. Preferably, the PI precursor has four, five or six monomers and is encoded by the nucleic acid molecule as hereinbefore described. The present invention also extends to the individual monomers comprising the precursor. The present invention also extends to a hybrid recombinant PI precursor molecule comprising at least two monomers from different PIs as hereinbefore described.

The isolated PI or PI precursor may be in recombinant form and/or biologically pure. By "biologically pure" is meant a preparation of PI, PI precursor and/or any mixtures thereof having undergone at least one purification step including ammonium sulphate precipitation, Sephadex chromatography and/or affinity chromatography. Preferably, the preparation comprises at least 20% of the PI, PI precursor or mixture thereof as determined by weight, activity antibody, reactivity and/or amino acid content. Even more preferably, the preparation comprises 30–40%, 50–60% or at least 80–90% of PI, PI precursor or mixture thereof.

The PI or its precursor may be naturally occurring or be a variant as encoded by the nucleic acid variants referred to above. It may also contain single or multiple substitutions, deletions and/or additions to its amino acid sequence or to non-proteinaceous components such as carbohydrate and/or lipid moieties.

The recombinant and isolated PI, PI precursor and mixtures thereof are useful as laboratory reagents, in the generation of antibodies, in topically applied insecticides as well as orally ingested insecticides.

The recombinant PI or PI precursor may be provided as an insecticide alone or in combination with one or more carriers or other insecticides such as the BT crystal protein.

The PI of the present invention is considered to have a defensive role in organs of the plant, for example, the stigma, against the growth or infection by pests and pathogens such as fungi, bacteria and insects. There is a need, therefore, to develop genetic constructs which can be used to generate transgenic plants capable of expressing the PI precursor where this can be processed into monomers of a monomeric PI itself.

Accordingly, another aspect of the present invention contemplates a genetic construct comprising a nucleic acid molecule comprising a sequence of nucleotides which encodes or is complementary to a sequence which encodes a type II serine PI precursor or monomer thereof from a plant wherein said precursor comprises at least three PI monomers and wherein at least one of said monomers has a chymotrypsin specific site and at least one of said other monomers has a trypsin specific site and said genetic sequence further comprises expression means to permit expression of said nucleic acid molecule, replication means to permit replication in a plant cell or, alternatively, integration means, to permit stable integration of said nucleic acid molecule into a plant cell genome. Preferably, the expression is regulated such as developmentally or in response to infection such as being regulated by an existing PI regulatory sequence. Preferably, the expression of the nucleic acid molecule is enhanced to thereby provide greater endogenous levels of PI relative to the levels in the naturally occurring plant. Alternatively, the PI precursor cDNA of the present invention is usable to obtain a promoter sequence which can then be used in the genetic construct or to cause its manipulation to thereby permit over-expression of the equivalent endogenous promoter. In another embodiment the PI precursor is a hybrid molecule as hereinbefore described.

Yet another aspect of the present invention is directed to a transgenic plant carrying the genetic sequence and/or nucleic acid molecule as hereinbefore described and capable of producing elevated, enhanced or more rapidly produced levels of PI and/or PI precursor or hybrid PI precursor when required. Preferably, the plant is a crop plant or a tobacco plant but other plants are usable where the PI or PI precursor nucleic acid molecule is expressable in said plant. Where the transgenic plant produces PI precursor, the plant may or may not further process the precursor into monomers. Alternatively, the genetic sequence may be part of a viral or bacterial vector for transmission to an insect to thereby control pathogens in insects which would consequently interrupt the transmission of the pathogens to plants.

In still yet another aspect of the present invention, there is provided antibodies to the PI precursor or one or more of its monomers. Antibodies may be monoclonal or polyclonal and are useful in screening for PI or PI precursor clones in an expression library or for purifying PI or PI precursor in a fermentation fluid, supernatant fluid or plant extract.

The genetic constructs of the present invention can also be used to populate the gut of insects to act against the insect itself or any plant pathogens therein or to incorporate into the gut of animals to facilitate the digestion of plant material.

The present invention is further described by reference to the following non-limiting Figures and Examples.

In the Figures:

FIG. 1 shows the nucleic acid sequence (SEQ ID NO. 2) of the pNA-PI-2 insert and the corresponding amino acid sequence (SEQ ID NO. 3) of the *N. alata* PI protein. The amino acid sequence is numbered beginning with 1 for the first amino acid of the mature protein. The signal sequence is encoded by nucleotides 1 to 97 and the amino acid residues have been assigned negative numbers. The reactive site residues of the inhibitor are boxed. The *N. alata* PI sequence contains six similar domains (domain 1, residues 1 to 58, domain 2, residues 59–116, domain 3, residues 117–174, domain 4, residues 175–232, domain 5, residues 233–290 and domain 6, residues 291–343).

FIG. 2 is a photographic representation showing a gel blot analysis of RNA from various organs of *N. alata*. Gel Blot of RNA isolated from organs of *N. alata* and from stigmas and styles of *N. tabacum* and *N. sylvestris*, hybridised with the cDNA clone NA-PI-2. St, stigma and style; Ov, ovaries; Po, pollen; Pe, petals; Se, sepals; L, non-wounded leaves; L4, leaves 4 h after wounding; L24, leaves 24 h after wounding; Nt, *N. tabacum* stigma and style; Ns, *N. sylvestris* stigma and style; Na HindIII restriction fragments of Lambda-DNA.

The NA-PI-2 clone hybridised to 2 mRNA species (1.0 and 1.4 kb). The larger mRNA was predominant in stigma and styles, whereas the smaller mRNA species was more dominant in other tissues. After high stringency washes, the 1.0 kb mRNA from stigma and style no longer hybridises to the NA-PI-2 probe.

Figure 3:
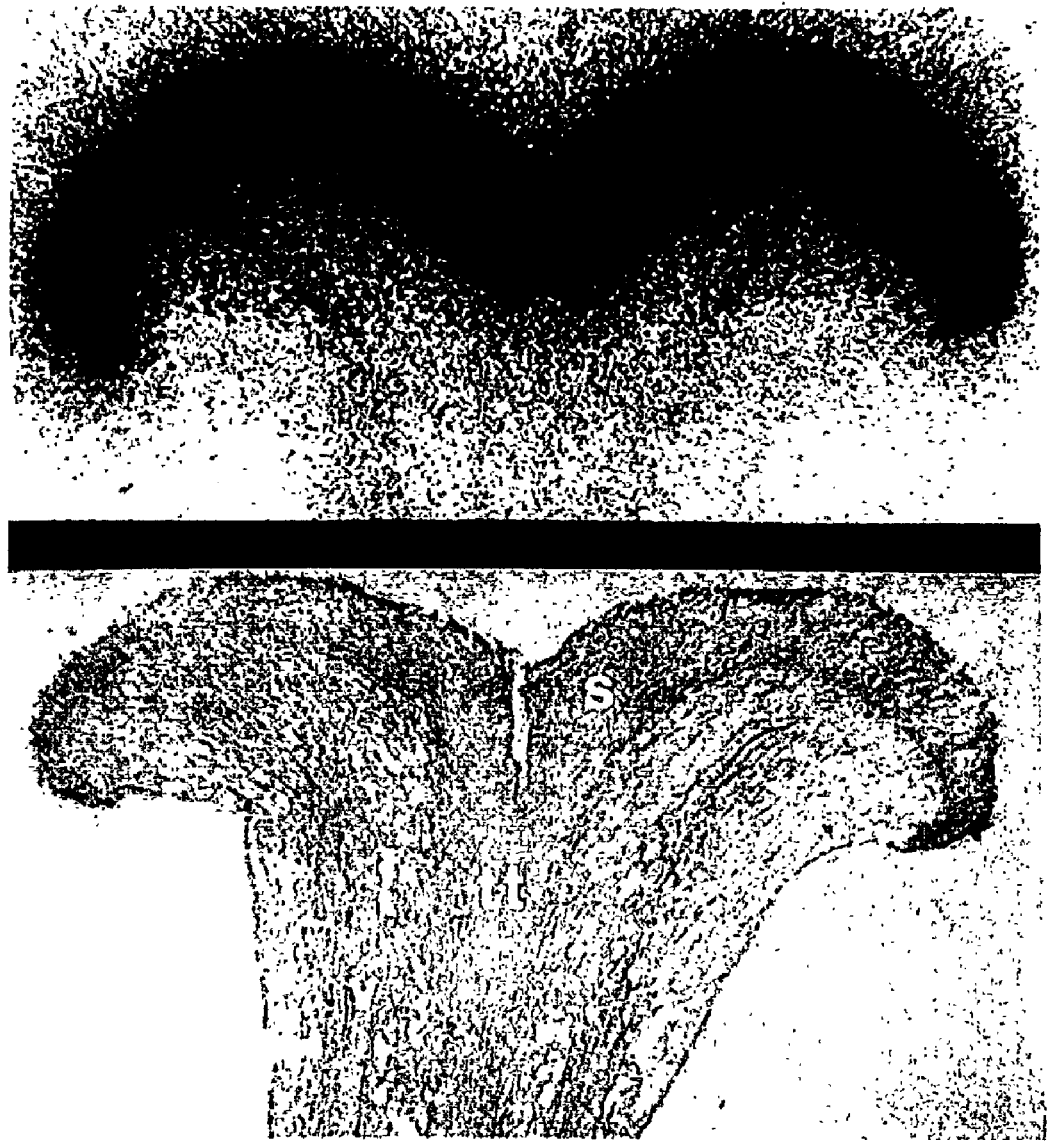

FIG. 3 is a photographic presentation depicting in situ localisation of RNA homologous to NA-PI-2 in stigma and style.
(a) Autoradiograph of a longitudinal cryosection through the stigma and style of a 1 cm long bud after hybridisation with the $^{32}$P-labelled NA-PI-2 cDNA probe.
(b) The same section as (a), stained with toluidine blue. c, cortex; v, vascular bundles; tt, transmitting tract; s, stigmatic tissue.

The cDNA probe labelled the cells of the stigma heavily and some hybridisation to the vascular bundles can be seen. There was no hybridisation to the epidermis, cortical tissue or transmitting tissue. Scale bars=200 μm.

Figure 4:
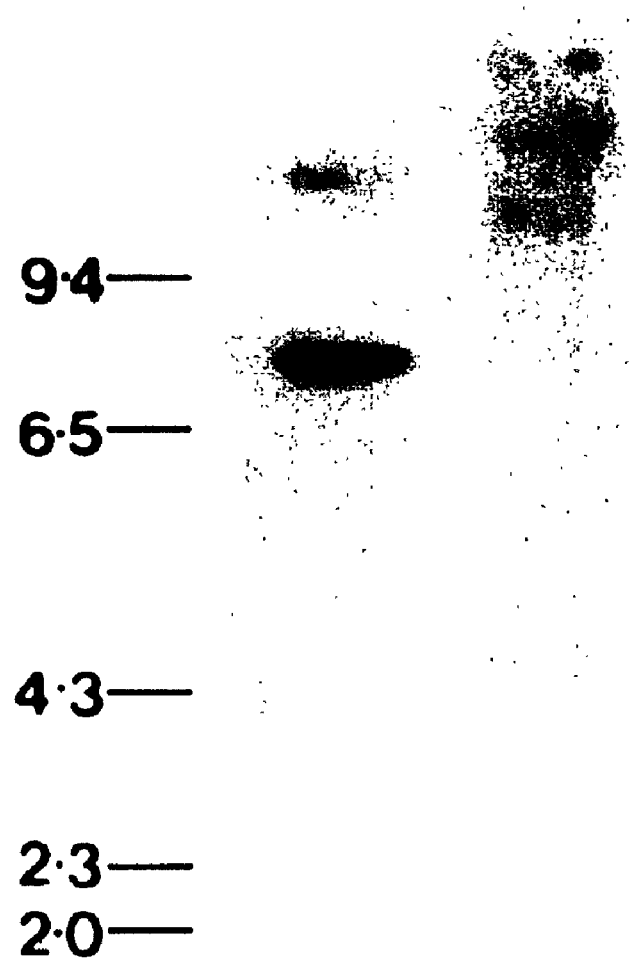

FIG. 4 is a photographic representation of a gel blot analysis of genomic DNA of N. alata. Gel blot analysis of N. alata genomic DNA digested with the restriction enzymes EcoRI or HindIII, and probed with radiolabelled NA-PI-2. Size markers (kb) are HindIII restriction fragments of Lambda-DNA.

EcoRI produced two hybridising fragments (11 kb and 7.8 kb), while HindIII gave three large hybridising fragments (16.6, 13.5 and 10.5 kb). The NA-PI-2 clone appears to belong to a small multigene family consisting of at least two members.

Figure 5A:
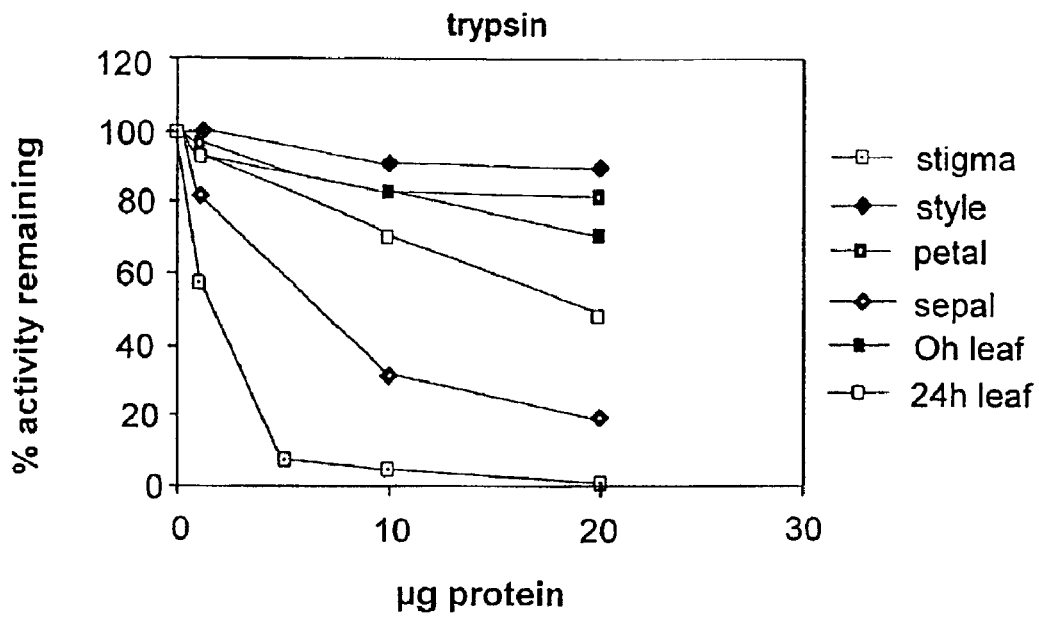
Figure 5B:
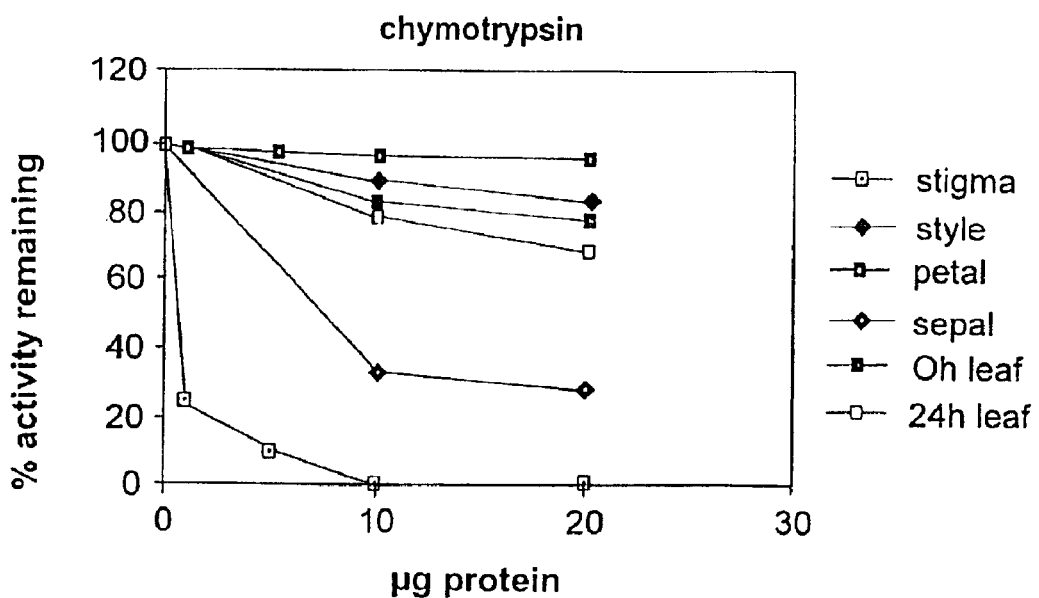

FIG. 5 is a graphic representation of PI activity in various organs of N. alata. Buffer soluble extracts from various organs were tested for their ability to inhibit trypsin and chymotrypsin. Stigma and sepal extracts were the most effective inhibitors of both trypsin (A) and chymotrypsin (B).

Figure 6A:
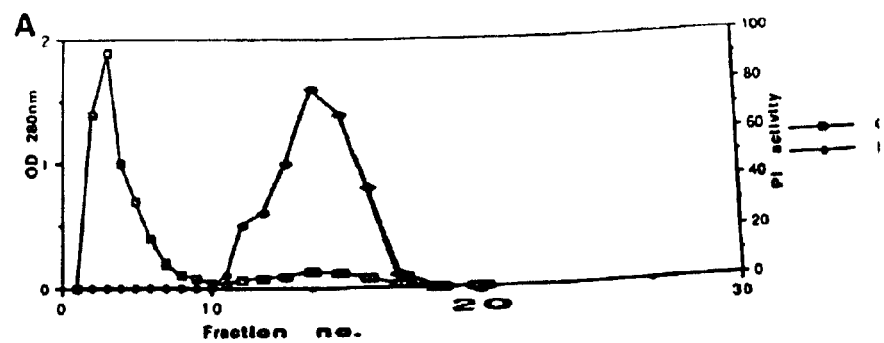
Figure 6B:

FIG. 6 depicts the steps of the purification of PI from N. alata stigmas.
(a) Sephadex G-50 gel filtration chromatography of ammonium sulphate precipitated proteins from stigma extracts. The PI activity eluted late in the profile.
(b) 20% w/v SDS-polyacrylamide gel (Laemmli, 1970) of fractions across the gel filtration column. The gel was silver stained and molecular weight markers (Pharmacia peptide markers) are in kilodaltons. A protein of about 6 kD (arrowed) coelutes with the proteinase inhibitor activity.
(c) Analysis of PI-containing fractions at different stages of the purification procedure, by SDS-PAGE. Lane 1, crude stigma extract (5 μg); Lane 2, stigma proteins precipitated by 80% w/v ammonium sulphate (5 μg); Lane 3, PI protein eluted from the chymotrypsin affinity column (1 μg).

The PI is a 6 kD protein and is a major component in unfractionated buffer soluble extracts from stigmas.

Figure 7A:
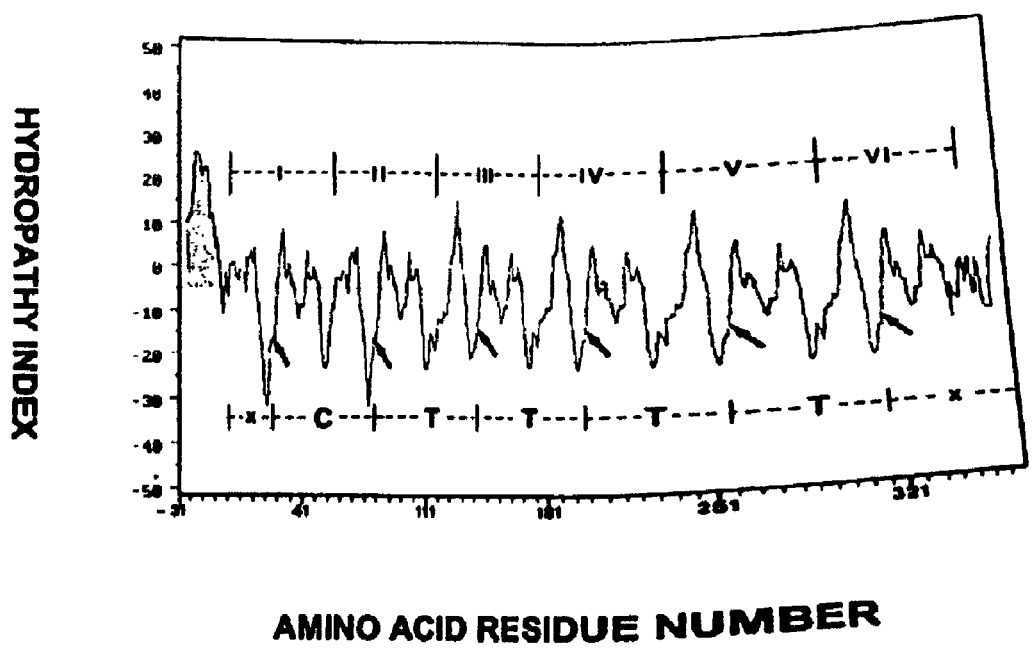
Figure 7:
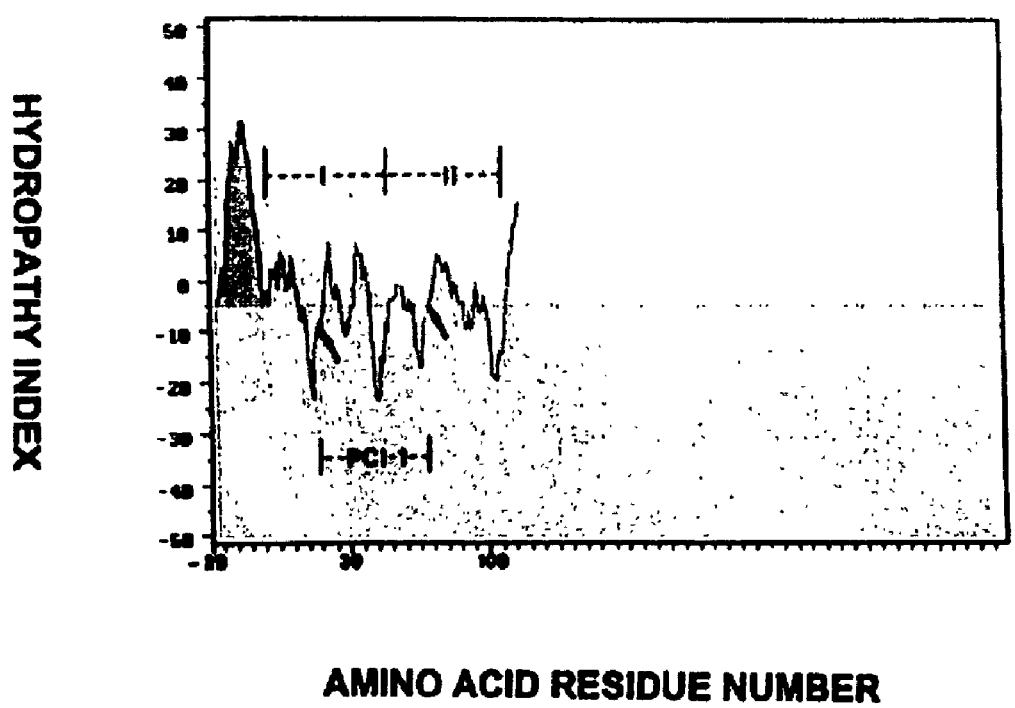
Figure 7C:
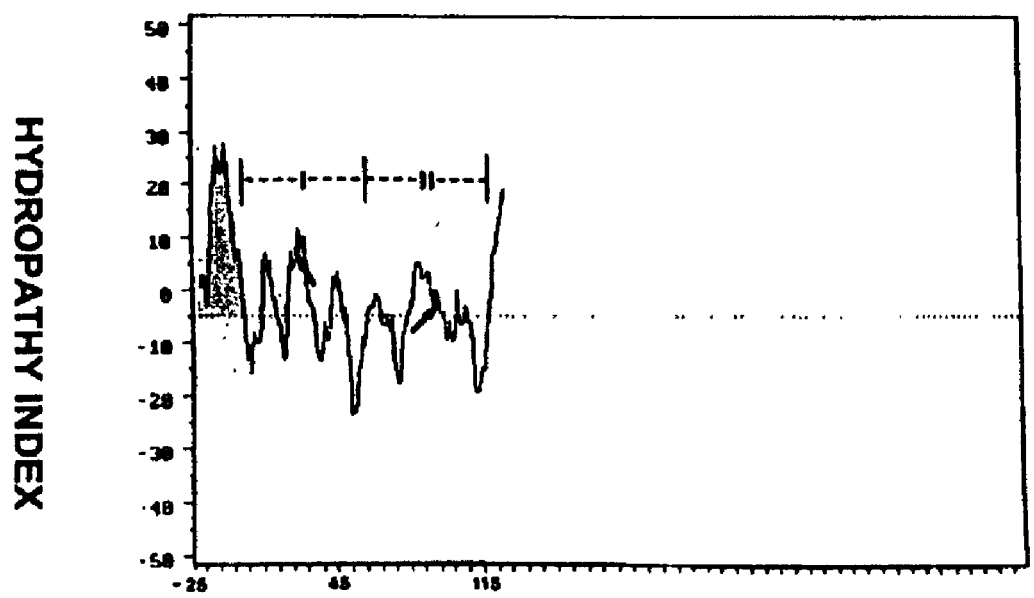

FIG. 7 is a graphical representation showing hydropathy plots of the PI proteins encoded by the NA-PI-2 clone from N. alata and the potato and tomato PI II cDNAs. Values above the line denote hydrophobic regions and values below the line denote hydrophilic regions. The putative signal peptides are shaded. The hydrophobicity profile was generated using the predictive rules of Kyte and Doolittle (1982) and a span of 9 consecutive amino acids.
(a) Hydropathy profile of the N. alata PI protein. The six repeated domains in the predicted precursor protein are labelled I–VI. The hydrophilic regions containing the putative cleavage sites for production of the 6 kD PI species are arrowed. The regions corresponding to the peptides that would be produced by cleavage at these sites are marked C for chymotrypsin inhibitor, T for trypsin inhibitor and x for the two flanking peptides.
(b) Hydropathy profile of the potato PI II protein. (Sanchez-Serrano et al., 1986). The two repeated domains in the PI II protein are labelled I and II. The putative cleavage sites for production of PCI-1 are arrowed (Hass et al., 1982) and the region spanned by PCI-1 is marked.
(c) Hydropathy profile of the polypeptide encoded by the tomato PI II cDNA (Graham et al., 1985). The two domains are labelled, I and II and the residues which would be potential processing sites are arrowed. These sites are not present in regions predicted to be hydrophilic and consequently a cleavage product is not marked.

Figure 8:
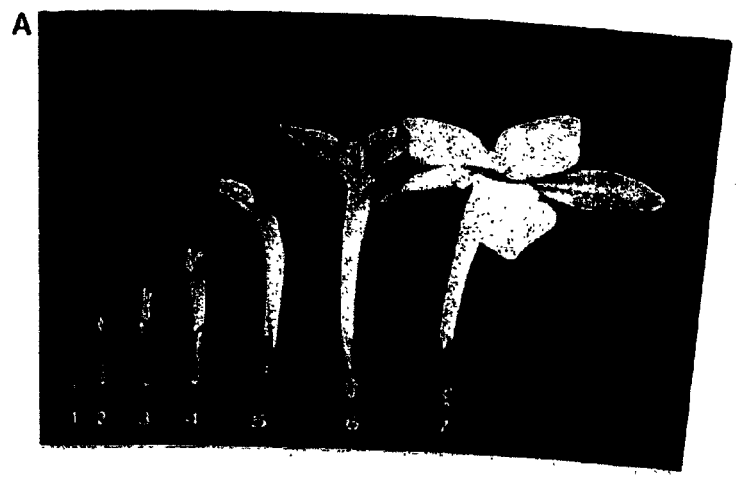
Figure 8:
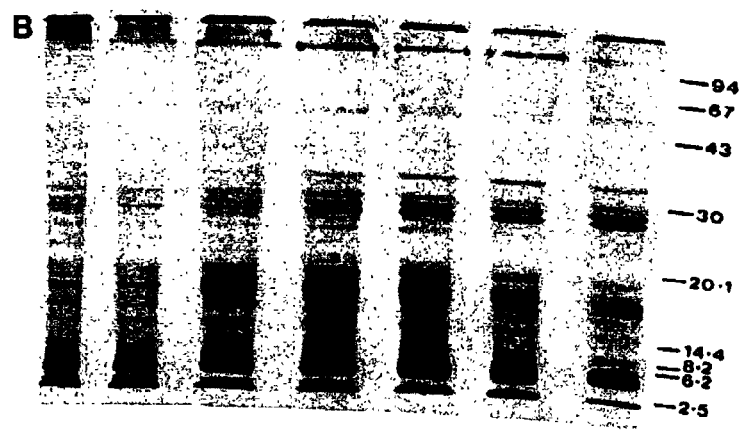
Figure 8:
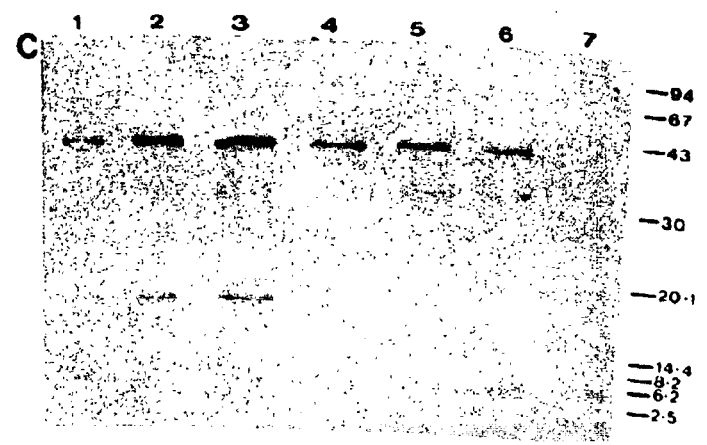

FIG. 8 shows an immunoblot analysis of the PI protein in stigmas of developing flowers.
(a) Developing flowers of N. alata.
(b) SDS-PAGE of stigma proteins at the stages of development shown in (a) 5 μg of each extract was loaded. The peptide gel was silver stained and molecular weight markers (LKB Low Molecular weight and Pharmacia peptide markers) are in kilodaltons.
(c) Immunoblot of a gel identical to (b), probed with anti-PI antiserum.

Stigmas from developing flowers contain four proteins of approximately 42 kD, 32 kD, 18 kD and 6 kD that bind to the anti-PI antibody. The 42 kD and the 18 kD components decrease in concentration as the flowers mature, while the 6 kD PI protein reaches a maximum concentration just before anthesis. The level of the 32 kD component, which runs as a doublet, does not alter significantly during flower development.

FIG. 9 shows the separation and identification of the 6 kD proteinase inhibitor species from N.alata stigmas A. Separation of the 6 kD PIs by reversed phase HPLC chromatography Four major peaks were obtained with retention times of about 15.5 min(peak1), 20.5 min(peak2), 22.5 min(peak3), 24 min(peak4). The peptides in each peak have been identified by a combination of N-terminal analysis and mass spectrometry. See B for description of C1 and T1–T4.

B. The five homologous peptides produced from the PI precursor protein: C1, chymotrypsin inhibitor, T1–T4 trypsin inhibitors. The solid bars represent the reactive sites of the inhibitors. The precursor protein is drawn minus the signal sequence. ▓ region of the six repeated domains (amino acids 1–343, FIG. 1). ▨ non-repeated sequence (amino acids 344–368, FIG. 1). The arrows point to the processing sites in the precursor protein.

C. The amino acid sequence of C1 and T1–T4 predicted from the cDNA clone and confirmed by N-terminal sequencing of the purified peptides. The amino acid at the carboxy-terminus of each peptide was obtained by accurate mass determination using an electro-spray mass spectrometer. The C1 and T1 inhibitors differ by five amino acids (bold). Two of these amino acids are located at the reactive site (underlined) and the other two to three reside at the carboxy-terminus. Peptides T2–T4 have changes in three amino acids (boxed) that are conserved between C1 and T1. Peptides T2 and T3 are identical to each other. Mass spectrometry was used to demonstrate that other forms of C1 and T1–T4 occur due to non-precise trimming at the N- and C-termini. That is, some forms are missing residue 1 or residue 53 and others are missing both residue 1 and 53 (see Table 2).

FIG. 10 shows the amino-acid sequence around the processing sites in the precursor PI protein.

The sequence in bold is the amino-terminal sequence obtained from the purified PI protein. The sequence labelled with negative numbers is the flanking sequence predicted from the cDNA clone. The predicted precursor protein contains six repeats of this sequence.

Figure 11A:
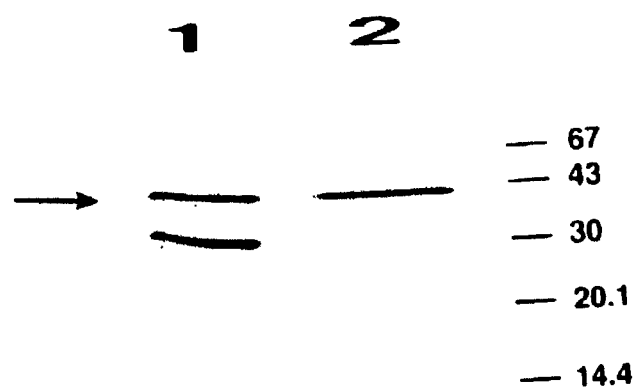
Figure 11B:

FIG. 11 shows the PI precursor produced in a baculovirus expression system and the products obtained after digestion of the affinity purified PI precursor by the endoproteinase Asp-N.

A. The PI precursor produced by the recombinant baculovirus. Immunoblot containing affinity and HPLC purified PI precursor from *N.alata* stigmas at the green bud stage of development (lane 1) and affinity purified PI precursor produced by the recombinant baculovirus (lane 2). Proteins were fractionated by electrophoresis on a 15% w/v SDS-polyacrylamide gel prior to electrophoretic transfer to nitrocellulose. The blot was incubated with the antibody raised in rabbits to the 6 kD PI species from stigmas. The recombinant virus produced an immunorective protein of 42 kD that is the same size as the PI precursor protein produced by stigmas (arrowed).

B. Cleavage of the PI precursor by endoproteinase Asp-N. 15% SDS-polyacrylamide gel stained with silver containing: 1, PI precursor, produced by baculovirus, incubated without enzyme. 2, enzyme incubated without precursor. 6 kD, PI peptides of about 6 kD purified from *N.alata* stigmas. 1 m, 5 m, 30 m, reaction products produced after 1, 5 and 30 minutes of incubation. 2 h and 24 h, reaction products after 2 and 24 h of incubation. Peptides of about 6–7 kD were detected within one minute of incubation of the precursor with the enzyme. After 24 h only peptides of 6–7 kD were detected. The bands smaller than 42 kD in track 1 are due to truncated forms of the precursor produced by premature termination of translation in the baculovirus expression system.

Figure 12:
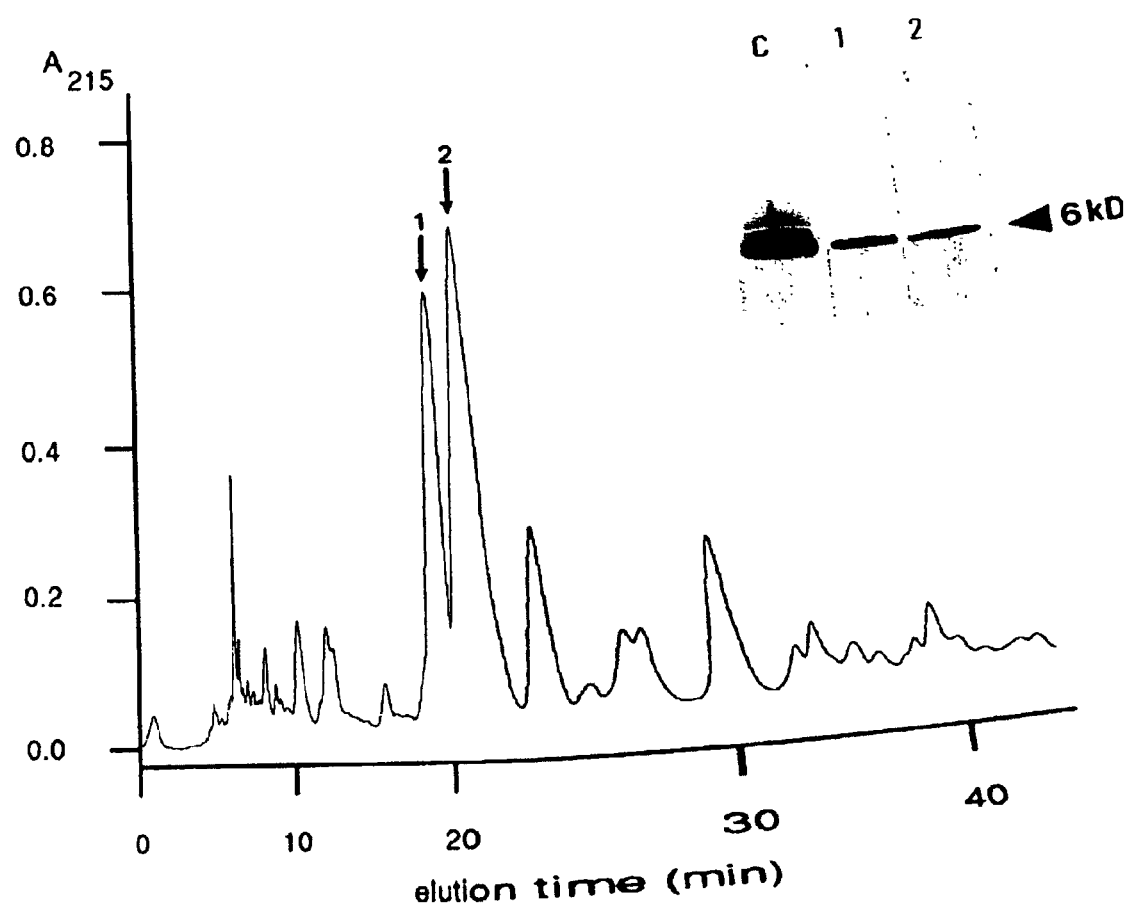

FIG. 12 Preparative chromatography by reversed phase HPLC of the peptides produced from the precursor by Asp-N digestion HPLC profile of peptides produced by Asp-N digestion of the PI precursor. The major peaks had a retention time of 19 min (termed Asp-Ni) and 21 min (termed Asp-N2). The peptides in these peak fractions (1 & 2) had a slightly slower mobility on SDS-PAGE than the 6 kD peptides from stigmas (C, inset). The proteinase inhibitory activity of Asp-N1 and Asp-N2 was tested against trypsin and chymotrypsin.

Figure 13A:
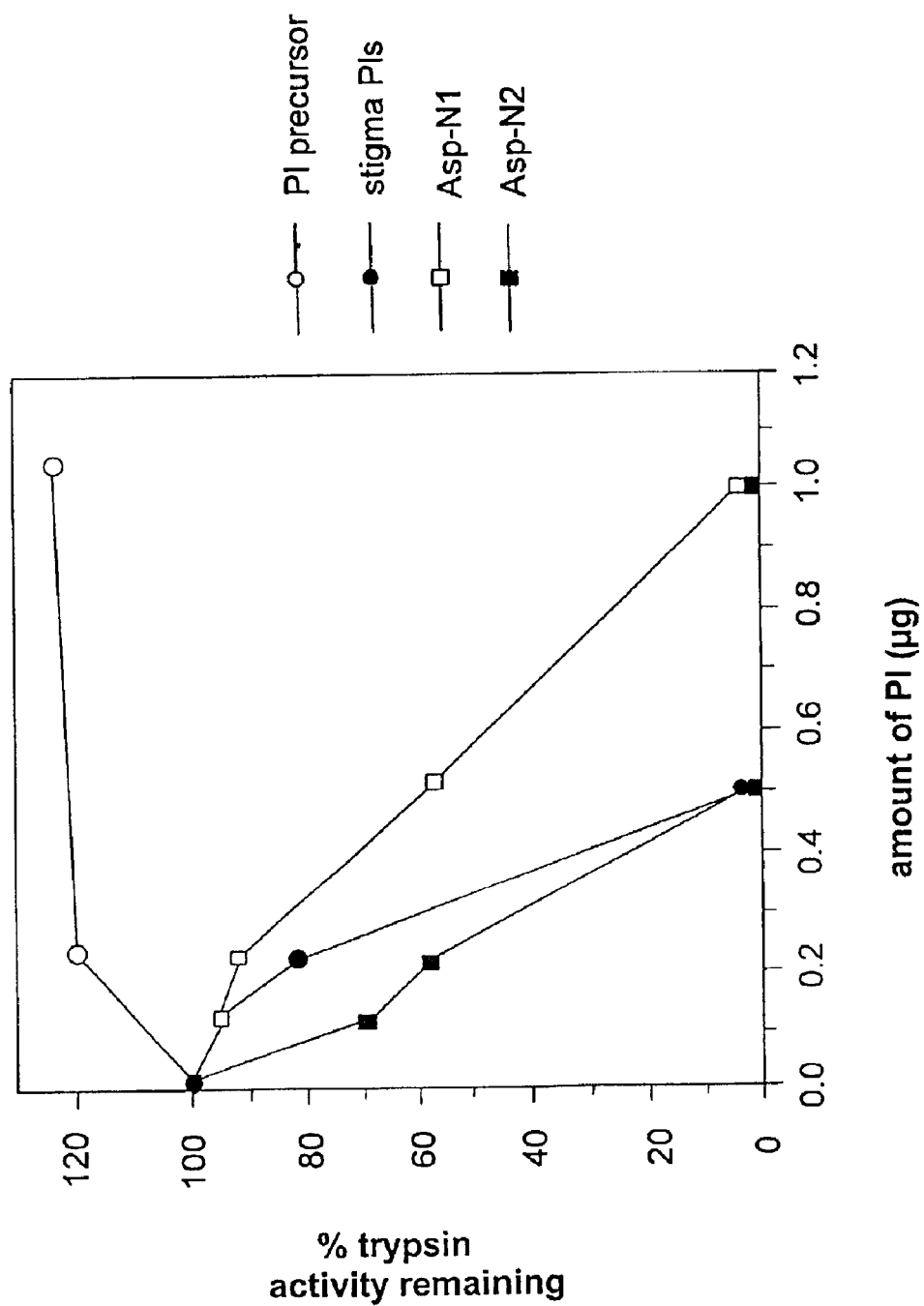
Figure 13B:
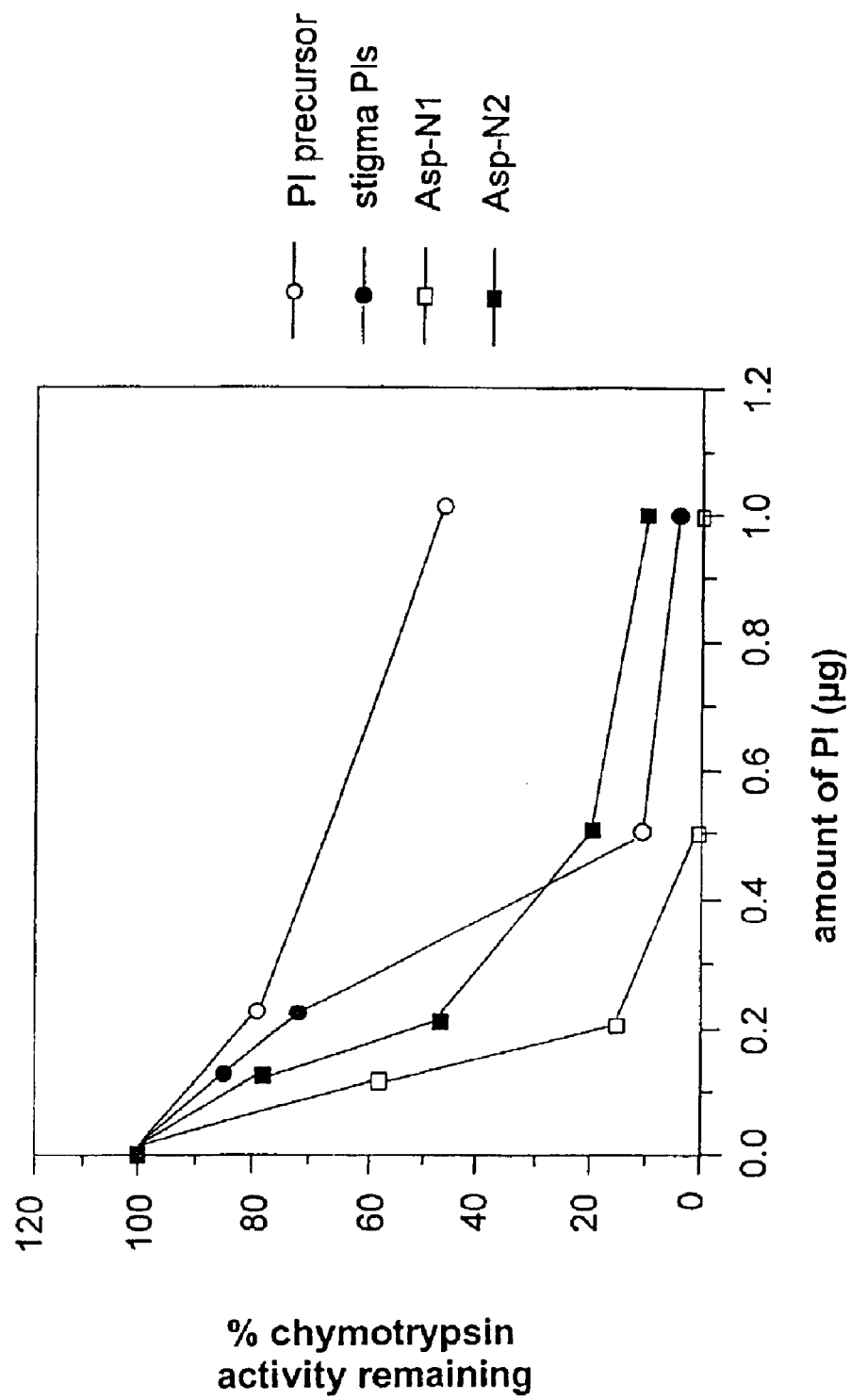

FIG. 13 shows a comparison of the trypsin and chymotrypsin inhibition activity of the PI precursor, PI peptides from stigmas and in vitro produced PI peptides from the PI precursor.

PI precursor or PI peptides (0–1.0 μg) were tested for their ability to inhibit 1.0 μg of trypsin or chymotrypsin as described in the materials and methods. Inhibitory activity is expressed as the percentage of proteinase activity remaining after the proteinase had been preincubated with the PI with 100% remaining activity taken as the activity of the proteinase preincubated with no PI. Experiments were performed in duplicate and mean values were plotted. Deviation from the mean was 8% or less.

Figure 14:
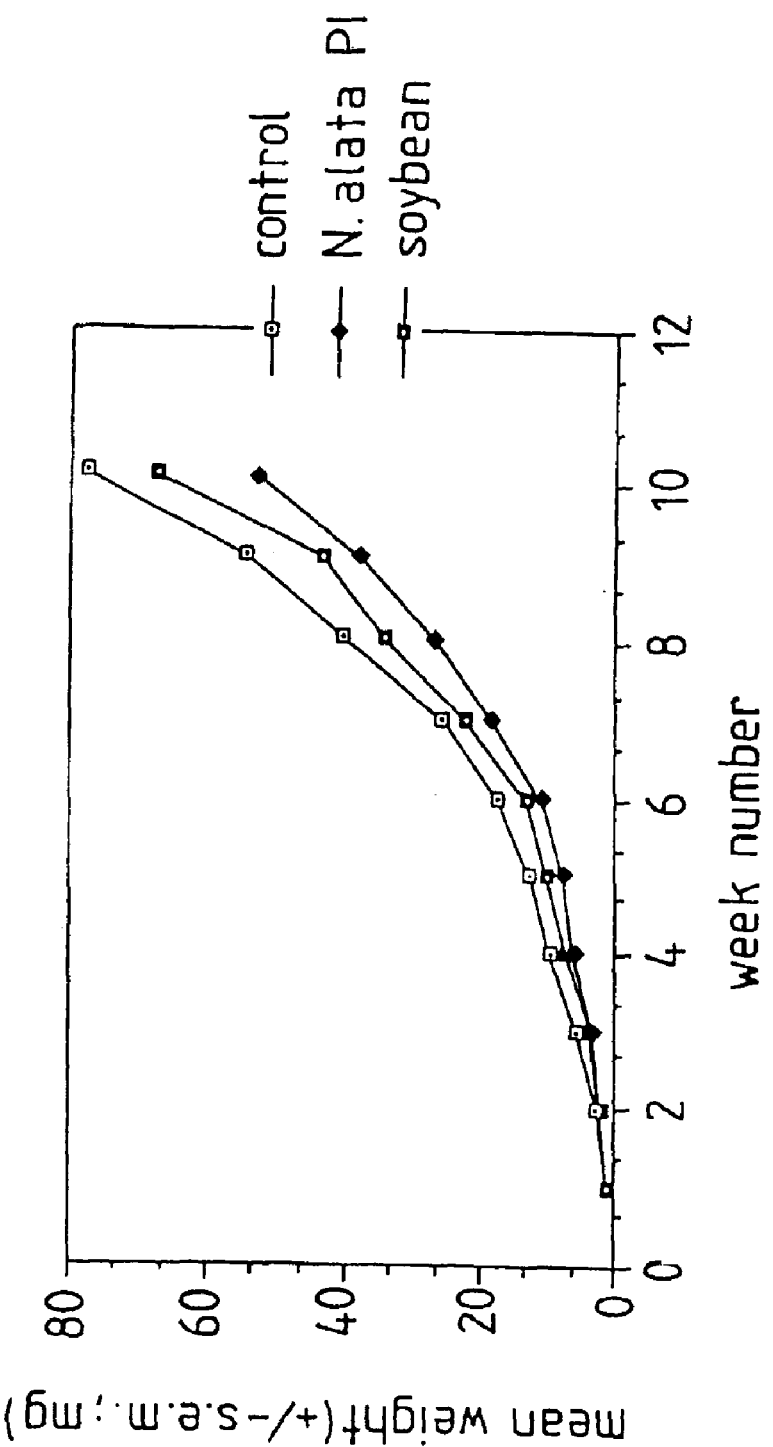

FIG. 14 is a graphical representation showing a growth curve for *T. commodus* nymphs reared on control artificial diet, soybean Bowman-Birk inhibitor and *N. alata* PI. The vertical axis represents the mean weight of the crickets in each treatment (+/− standard error) in mg. The horizontal axis represents the week number. The crickets reared on the *N. alata* PI showed a lower mean weight than those reared on both the control diet and the diet containing the soybean inhibitor, throughout the experiment.

SUMMARY OF SEQ ID NOs

| | |
|---|---|
| SEQ ID NO.1 | Nucleotide coding region of *N. alta* P1 precursor |
| SEQ ID NO.2 | Full length nucleotide sequence of *N. alata* PI precursor |
| SEQ ID NO.3 | Amino acid sequence corresponding to SEQ ID NO.1 |
| SEQ ID NO.4 | Residues 1–24 of SEQ ID NO.2 (pepide 1) |
| SEQ ID NO.5 | Residues 25–82 of SEQ ID NO.2 (peptide 2) |
| SEQ ID NO.6 | Residues 83–140 of SEQ ID NO.2 (peptide 3) |
| SEQ ID NO.7 | Residues 141–198 of SEQ ID NO.2 (peptide 4) |
| SEQ ID NO.8 | Residues 199–256 of SEQ ID NO.2 (peptide 5) |
| SEQ ID NO.9 | Residues 257–314 of SEQ ID NO.2 (peptide 6) |
| SEQ ID NO.10 | Residues 315–368 of SEQ ID NO.2 (peptide 7) |
| SEQ ID NO.11 | N-terminal amino acid sequence of 6kD PI protein |
| SEQ ID NO.12 | N-terminal amino acid sequence of 6kD PI protein |

EXAMPLE 1

1. Materials and Methods

Plant Material

*Nicotiana alata* (Link et Otto) plants of self-incompatibility genotype $S_1S_3$, $S_3S_3$ and $S_6S_6$ were maintained under standard glasshouse conditions as previously described (Anderson et al., 1989). Organs were collected directly into liquid Nitrogen to avoid induction of a wound response and stored at −70° until required. To study the effect of wounding on gene expression, leaves were wounded by crushing across the mid-vein with a dialysis clip. Leaves were collected 4 and 24 hours after wounding.

Identification and Sequencing of a cDNA Clone Encoding PI

Polyadenylated RNA was prepared from stigmas and styles, isolated from mature flowers of *N. alata* (genotype $S_3S_3$), and used to construct a cDNA library in Lambda gt10 (Anderson et al., 1989). Single stranded $^{32}$P-labelled cDNA was prepared from mRNA from stigmas and styles of *N. alata* (genotype $S_3S_3$ and $S_6S_6$) and used to screen the library for highly expressed clones which were not S-genotype specific (Anderson et al., 1989). Plaques which hybridised strongly to cDNA probes from both S-genotypes were selected and assembled into groups on the basis of cross-hybridisation. The longest clone of each group was subcloned into M13mp18 and pGEM 3zf+, and sequenced using an Applied Biosystems Model 373A automated sequencer. Both dye primer and dye terminator cycle sequencing chemistries were performed according to standard Applied Biosystems protocols. Consensus sequences were generated using SeqEd™ sequence editing software (Applied Biosystems). The GenBank database was searched for sequences homologous to these clones. Because of the high degree of sequence similarity between the six domains of the *N. alata* PI clone, sequencing primers were made to non-repeated 3' sequences (nucleotides 1117–1137, 1188–1203 and 1247–1267), and to a 5' sequence before the start of the repetitive regions (nucleotides 74–98). In addition, the pNA-PI-2 insert was restricted with endonuclease HaeIII, which cut at nucleotides 622 and 970 to produce three fragments. The fragments were subcloned into pGEM7zf+ and sequenced in both directions, using the M13 forward and reverse primers. The repetitive nature of the pNA-PI-2 insert rendered it unstable in both phagemid and plasmid vectors when cultures were grown longer than 6 hours.

RNA Gel Blot Analysis

Total RNA was isolated and separated on a 1.2% w/v agarose/formaldehyde gel as previous described (Anderson et al., 1989). The RNA was transferred to Hybond-N (Amersham) and probed with the insert from pNA-PI-2 labelled with $^{32}$P using random hexanucleotides ($1\times10^8$ cpm $\mu g^{-1}$; $1\times10^7$ cpm ml$^{-1}$)(Feinberg and Vogelstein, 1983). Prehybridisation and hybridisation, at 68° C., were as described by Anderson et al. (1989). The filters were washed in 2×SSC, 0.1% w/v SDS or 0.2×SSC, 1% w/v SDS at 68° C.

In situ Hybridisation

In situ hybridisation was performed as described by Cornish et al., 1987. The probe was prepared by labelling the insert from pNA-PI-2 (100 ng) to a specific activity of $10^8$ cpm $\mu g^{-1}$ by random hexanucleotide priming (Feinberg and Vogelstein, 1983). The labelled probe was precipitated, and resuspended in hybridisation buffer (50 $\mu$l), and 5 $\mu$l was applied to the sections. The sections were covered with coverslips, and incubated overnight at 40° C. in a closed box containing 50% v/v form amide. After incubation, sections were washed sequentially in 4×SSC at room temperature, 2×SSC at room temperature, and 1×SSC at 40° C. for 40 min. The slides were dried and exposed directly to X-ray film (Cronex MRF 32, Dupont) at room temperature, overnight. Hybridised sections were counterstained with 0.025% w/v toluidine blue in H$_2$O, and mounted in Eukitt (Carl Zeiss, Freilburg, FRG). Autoradiographs were transposed over sections to give the composites shown.

DNA Gel Blot Analysis

Genomic DNA was isolated from young leaves of N. alata by the procedure of Bernatzky and Tanksley (1986). DNA (10 $\mu$g) was digested to completion with the restriction endonucleases EcoRI or HindIII, separated by electrophoresis on a 0.9% w/v agarose gel, and transferred to Hybond-N (Amersham) by wet blotting in 20×SSC. Filters were probed and washed as described for RNA blot analysis.

Preparation of Protein Extracts

Soluble proteins were extracted from plant material by freezing the tissue in liquid N$_2$, and grinding to a fine powder in a mortar and pestle. The powdered tissue was extracted in a buffer consisting of 100 mM Tris-HCl, pH 8.5, 10 mM EDTA, 2 mM CaCl$_2$, 14 $\mu$M β-mercaptoethanol. Insoluble material was removed by centrifugation at 10,000 g for 15 min. Protein concentrations were estimated by the method of Bradford (1976) with Bovine Serum Albumin (BSA) as a standard.

Proteinase Inhibition Assays

Protein extracts and purified protein were assayed for inhibitory activity against trypsin and chymotrypsin as described by Rickauer et al. (1989). Inhibitory activity was measured against 1 $\mu$g of trypsin (TPCK-treated; Sigma) or 3 $\mu$g of chymotrypsin (TLCK-treated; Sigma). The rate of hydrolysis of synthetic substrates N-α-P-tosyl-L-arginine methyl ester (TAME) and N-benzoyl-L-tyrosine ethyl ester (BTEE) by trypsin and chymotrypsin, respectively, were taken as the uninhibited activity of the enzymes. Inhibitory activity of the extract was expressed as the percentage of control protease activity remaining after the protease had been pre-incubated with the extract. The PI peptides from stigma, PI precursor and Asp-N processed peptides were assayed for inhibitory activity as described by Christeller et al (1989).

Purification of the N. alata PI Protein

Stigmas (1000; 10 g) were ground to a fine powder in liquid N$_2$, and extracted in buffer (100 mM Tris-HCl, pH8.5, 10 mM EDTA, 2 mM CaCl$_2$, 14 $\mu$M β-mercaptoethanol, 4 ml/g tissue). To concentrate the extract prior to the first purification step, gel filtration, the inhibitory activity was precipitated with 80% w/v ammonium sulphate, the concen tration required to precipitate all the proteinase inhibitory activity.

The ammonium sulphate pellet was resuspended in 5 ml of 0.15M KCl, 10 mM Tris-HCl, pH 8.1, and loaded onto a Sephadex G-50 column (2 cm×100 cm) equilibrated with the same buffer. The fractions (10 ml) eluted from this column and containing proteinase inhibitory activity were pooled and applied to an affinity column of Chymotrypsin-Sepharose CL4B [100 mg TLCK-treated α-chymotrypsin (Sigma) cross-linked to 15 ml Sepharose CL4B (Pharmacia) by manufacturers instructions]. The column was washed with 10 volumes of 0.15M KCl/10 mM Tris-HCl, pH 8.1, prior to elution of bound proteins with 7 m urea, pH 3 (5 ml fractions). The eluate was neutralised immediately with 200 $\mu$l 1M Tris-HCl pH 8, and dialyzed extensively against deionised H$_2$O.

Amino Acid Sequence Analysis

Purified PI protein was chromatographed on a reverse phase HPLC microbore column prior to automated Edman degradation on a gas phase sequencer (Mau et al., 1986). Phenylthiohydantoin (PTH) amino acids were analysed by HPLC as described by Grego et at (1985).

Production of a Polyclonal Antiserum to the N. alata PI

The purified proteinase inhibitor (FIG. 6c, lane 3) was conjugated to a carrier protein, keyhole limpet haemocyamn (KLH) (Sigma), using glutaraldehyde, as follows. 1 mg of PI protein was dissolved in 1.5 ml H$_2$O, and mixed with 0.3 mg KLH in 0.5 ml of 0.4M phosphate buffer, pH7.5. 1 ml of 20 mM glutaraldehyde was added dropwise over 5 min, with stirring at room temperature. The mixture was stirred for 30 min at room temperature, 0.25 ml of glycine was added, and the mixture was stirred for a further 30 min. The conjugated protein was then dialyzed extensively against normal saline (0.8% w/v NaCl). The equivalent of 100 $\mu$g of PI protein was used for each injection. Freund's complete adjuvant was used for the first injection, and incomplete adjuvant for two subsequent booster injections. The IgG fraction of the antiserum was separated on Protein A Sepharose (Pharmacia) according to manufacturer's instructions.

Protein Gel Blot Analysis

Protein extracts were electrophoresed in 15% w/v SDS-polyacrylamide gels (Laemmli, 1970) and transferred to nitrocellulose in 25 mM Tris-HCl, 192 mM glycine, 20% v/v methanol, using a BioRad Trans-Blot$^R$Semi-dry electrophoretic transfer cell (12V, 20 min). Loading and protein transfer were checked by staining the proteins on the membranes with Ponceau S (Harlow and Lane, 1988). Membranes were blocked in 3% w/v bovine serum albumin for 1 h, and incubated with the anti-PI antibody (2 $\mu$g/ml in 1% w/v BSA, Tris Buffered Saline) overnight at room temperature. Bound antibody was detected using biotinylated donkey anti-rabbit IgG (1/1500 dilution, Amersham) and the Amersham Biotin-Streptavidin system according to procedures recommended by the manufacturer.

Proteolysis of the PI Precursor by Endoproteinase Asp-N

Affinity-purified PI precursor (1.25 mg) was incubated at 37° C. with endoproteinase Asp-N (2 $\mu$g) in 100 mM NH$_4$HCO$_3$, pH 8.5 in a total volume of 1 ml for 48 h. Reaction products were separated by reversed-phase HPLC using an analytical Brownlee RP-300 Aquapore column (C8, 7 $\mu$m, 4.6×100 mm). The column was equilibrated in 0.1% v/v TFA and peptides were eluted with the following program: 0–25% B (60% v/v acetonitrile in 0.089% v/v TFA) applied over 5 min, followed by a gradient of 25–42% B over the next 40 min, and ending with a gradient of 42–100% B over 5 minutes. The flow rate was 1.0 ml/min and peptides were detected by absorbance at 215 nm. Each peak was collected manually and freeze dried. Concentration was estimated by response obtained with each peak on the UV detector at 215 nm.

2. Cloning of PI Precurser Gene

Isolation and Characterisation of the PI cDNA Clone

A cDNA library, prepared from mRNA isolated from the stigmas and styles of mature flowers of N. alata, was screened for clones of highly expressed genes which were not associated with self-incompatibility genotype. Clones encoding a protein with some sequence identity to the type II proteinase inhibitors from potato and tomato (Thornburg et al., 1987; Graham et al., 1985) were selected. The largest clone, NA-PI-2, is 1360 base pairs long with an open reading frame of 1191 nucleotides. The nucleic acid sequence (SEQ ID NO. 2) and the predicted amino acid sequence (SEQ ID NO. 3) of the N. alata clone, NA-PI-2 is shown in FIG. 1. There are no potential N-glycosylation sites.

Surprisingly, the N. alata cDNA clone encodes a protein with six repeated domains that have high, but not perfect, sequence identity (FIG. 1). Each of these domains contains a potential reactive site which is highlighted in FIG. 1. The residues at the putative reactives sites of the N. alata PI are consistent with the inhibitor having two sites which would specifically inhibit chymotrypsin (Leu5-Asn6, Leu63-Asn64) and four sites specific for trypsin (Arg121-Asn122, Arg179-Asn180, Arg237-Asn238 and Arg295-Asn296).

To ensure that the repeat structure of NA-PI-2 was not due to a cloning artifact, three additional cDNA clones were sequenced, and found to be identical to NA-PI-2.

Table 1 is a comparison of the percentage amino acid identity of the six domains of the PI precursor.

Temporal and Spatial Expression of the PI mRNA

Total RNA, isolated from various tissues of N. alata, was probed with the PI cDNA clone in the RNA gel blot analyses shown in FIG. 2. Two hybridising messages of 1.0 and 1.4 kb were present in total RNA isolated from styles (including stigmas). Only the larger message, which was predominant in this tissue, is of sufficient size to encode the cDNA clone NA-PI-2 (1.4 kb). The smaller message is not detected with the cDNA probe at higher stringency. An homologous message of approximately 1.4 kb was also present in RNA isolated from the styles of N. tabacum and N. sylvestris (FIG. 2).

In the other floral organs (except pollen), both messages were detectable at low levels, however, the smaller RNA species appeared more abundant. There was no hybridisation to pollen RNA. No hybridising species were evident in leaf RNA, but two species, 1.0 and 1.4 kb were detected 24 hours after mechanical wounding. The smaller message (1.0 kb) was more abundant in this case.

In situ hybridisation of radiolabelled N. alata PI cDNA to longitudinal sections of styles from immature (1 cm long) buds is shown in FIG. 3. RNA homologous to the cDNA clone bound strongly to cells of the stigma and weakly to vascular bundles. No hybridisation was detected in the cortical tissue, transmitting tract tissue, or epidermis of the style. The same pattern of hybridisation was observed in mature receptive flowers. Control sections treated with ribonuclease A prior to hybridisation were not labelled.

Genomic DNA Blot Analysis

The cDNA clone NA-PI-2, was used as a probe on the DNA gel blot shown in FIG. 4 which contained genomic DNA, digested with either EcoRI or HindIII. EcoRI produced two hybridising fragments (11 kb and 7.8 kb) and HindIII produced three large hybridising fragments (16.6, 13.5 and 10.5 kb).

Distribution of PI Activity in Various Tissues of N. alata

The inhibition of trypsin and chymotrypsin by crude extracts of various organs of N. alata is shown in FIG. 5. Stigma extract was the most effective inhibitor of both trypsin and chymotrypsin. The stigma extracts had up to eight times more inhibitory activity than sepal extracts, and more than 20 times more activity than extracts from styles, petals, leaves and wounded leaves.

Purification of PI from N. alata Stigmas

Figure 6C:
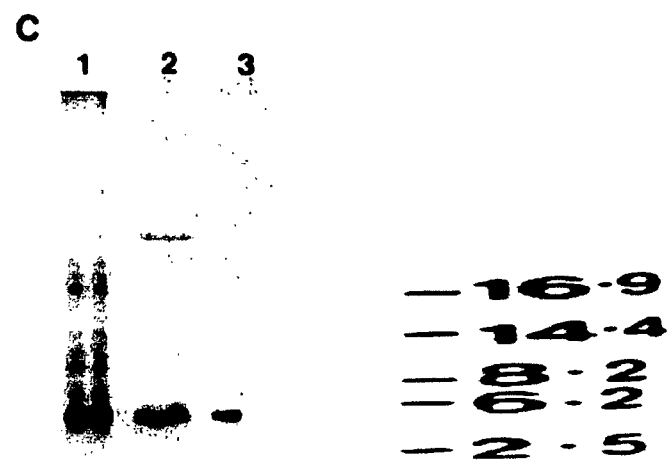

Stigmas of N. alata were extracted in buffer and the inhibitory activity was concentrated by precipitation with 80% w/v ammonium sulphate. The precipitate was redissolved and fractionated by gel filtration on Sephadex G-50. Most of the protein in the extract eluted early in the profile illustrated in FIGS. 6a and 6b, relative to the proteinase inhibitor. Fractions with proteinase inhibitor activity were pooled and applied to an affinity column of chymotrypsin-Sepharose. The PI activity co-eluted with a protein of about 6 kD, which appeared to migrate as a single band on the 20% SDS-polyacrylamide gel shown in FIG. 6c. The purity of the PI at various stages of purification was assessed by SDS-PAGE (FIG. 6c). The purified inhibitor represented approximately 50% of the inhibitory activity present in the crude extract.

Amino Acid Sequence of the N-terminus of the 6 kD PI Protein

The N-terminal amino acid sequence DRICTNCCAG(T/K)KG (SEQ ID NO. 11; SEQ ID NO. 12, respectively) was obtained from the purified PI protein. This sequence of amino acids corresponds to six regions in the deduced sequence of the cDNA clone, starting at positions 25, 83, 141, 199, 257 and 315 in FIG. 1. At position 11 of the N-terminal sequence, both threonine and lysine were detected.

This is consistent with the purified inhibitor comprising a mixture of six peptides beginning with the sequences underlined in FIG. 1, as the first two peptides contain threonine at this position, while the other four peptides have lysine at this position. The position of these peptides relative to the six repeated domains in the predicted precursor protein is illustrated in FIG. 7. Five of the six predicted 6 kD peptides, contain a reactive site for either chymotrypsin or trypsin (FIGS. 1 and 7). The sixth potential peptide is four aminoacids shorter than the other five peptides (fifty eight aminoacids) and may not be active, as it does not contain an inhibitory site. The peptide from the N-terminus (x in FIG. 7) has a potential chymotrypsin reactive site but is much shorter (24 amino acids).

Distribution of the PI Protein in N. alata

A polyclonal antiserum was raised to the purified PI protein conjugated to keyhole limpet haemocyanin. The antibody reacted strongly with the purified 6 kD PI protein in immunoblot analyses and bound only to a 6 kD and a 32 kD protein, which appears as a doublet, in total stigma and style extracts from mature flowers. FIG. 8 is an immunoblot containing protein extracts of stigmas from flowers at different stages of development (1 cm long buds to mature flowers) probed with the anti-PI antiserum. Larger cross reacting proteins of approximately 18 kD, and 42 kD were detected in buds from 1 cm to 5 cm in length in addition to the 6 kD and the 32 kD protein. The 18 kD and 42 kD proteins decreased in concentration with maturity, while the 6 kD protein reached a peak concentration just before anthesis. The concentration of the 32 kD protein remained relatively constant during flower maturation.

TABLE 1

|  |   | N. alata PI |     |     |     |     |     |
|---|---|---|---|---|---|---|---|
|  |   | 1 | 2 | 3 | 4 | 5 | 6 |
| N. alata | 1 |   | 100 | 88 | 88 | 90 | 79 |
|  | 2 |   |   | 88 | 88 | 90 | 79 |
|  | 3 |   |   |   | 97 | 95 | 86 |
|  | 4 |   |   |   |   | 98 | 90 |
|  | 5 |   |   |   |   |   | 90 |
|  | 6 |   |   |   |   |   |   |

EXAMPLE 2

Purification and Identification of PI Monomers

1. Materials and Methods

Separation of the 6 kD PI Species by Reversed Phase Chromatography

Stigmas (21,000) were ground and extracted as described for purification of the PI protein. After gel filtration on a Sephadex G-50 gel filtration column (5 cm×800 cm, 3000 stigmas per separation) the peptides were lyophilized and applied to a Brownlee RP-300 C8 Reversed-phase column, 10×250 mm, on a Beckman HPLC system Gold, and eluted with 0.1% v/v Trifluoroacetic acid (TFA) and an acetonitrile gradient (0–10% over 5 mins, 10–25% over 40 mins and 25–60% over 10 mins), at 5 ml/min. Peak fractions, designated fraction 1, 2, 3 and 4 were collected and freeze dried.

Electrospray Mass Spectrometry

On line mass spectrometric analysis of HPLC eluates was performed by application of 20 pmoles of each PI preparation (fraction 1, 2, 3 & 4) in 2 µl of water onto a Brownlee RP-300 C8 reversed-phase column (15×0.20 mm internal diameter fused-silica capillary column) on a modified Hewlett-Packard model HP1090L liquid chromatograph and elution with a linear gradient of acetonitrile (0.05% v/v TFA to 0.045% v/v TFA/60% v/v acetonitrile in 30 min.) at a flow rate of 1 µl/min and a column temperature of 25° C. The eluant was monitored at 215 nm using a Spectral Physics forward optics scanning detector with a 6-mm pathlength U-shaped axial beam capillary flow cell (LC Packings, Netherlands). Mass spectra were acquired on a Finnigan-Mat triple quadrupole mass spectrometer (modelTSQ-700, San Jose, Calif.) equipped with an electrospray ionisation (ESI) source (Analytica, Branford, Conn.). The electrospray needle was operated in positive ion mode at a voltage differential of −4 kV. The sheath liquid was 2-methoxyethanol delivered at 1 µl/min via a syringe drive (Harvard Apparatus, South Natick, Mass.). The nitrogen drying gas conditions were as follows: heater temperature, 275° C.; pressure, 15 psi; flow rate, −15 stdL/min. The nitrogen sheath gas was supplied at 33 psi. Gaseous nitrogen was obtained from a boiling liquid nitrogen source. Peptides were introduced into the ESI source at 1.0 µl/min by on-line capillary RP-HPLC as described above. Spectra were acquired scanning from m/z 400 to 2000 at a rate of 3 sec. Data collection and reduction were performed on a Dec5100 computer using Finnigan BIOMAS™ software.

2. Results

Figure 9A:
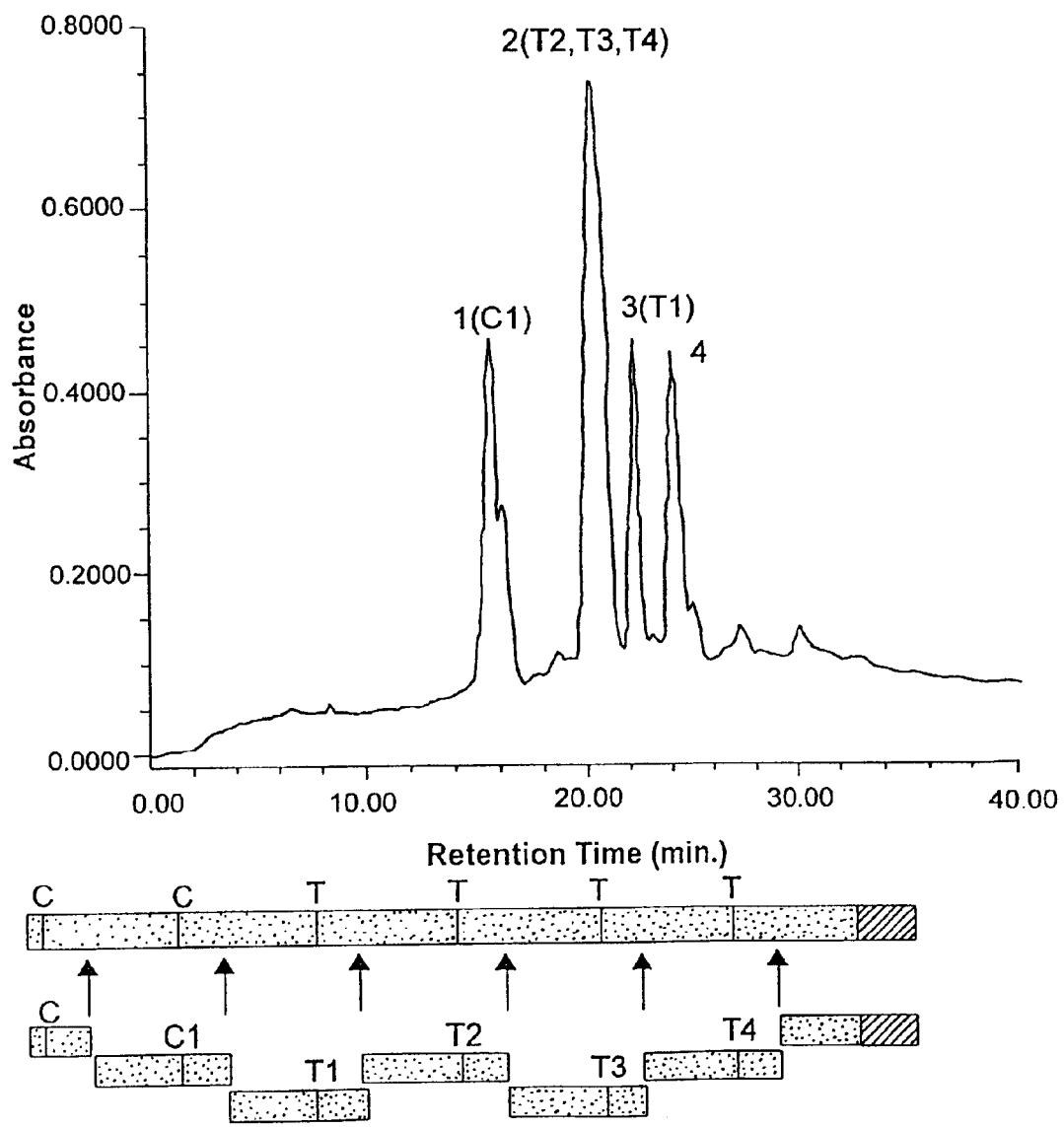

Separation and Identification of the Individual 6 kD PI Species from N.alata Stigmas The five of the six peptides of about 6 kD that were predicted to be present in the purified 6 kD PI preparation have been separated from each other by reversed-phase HPLC chromatography. Four peaks were obtained (FIG. 9a) and the peptides within each peak were identified by electrospray mass spectrometry (Table 2). The peptides have been designated C1, T1, T2, T3, and T4 according to their position in the PI precursor and the presence of a chymotrypsin or trypsin reactive site (FIG. 9b). The first HPLC peak (FIG. 9a) corresponds to the chymotrypsin inhibitor C1, the second peak is composed of a mixture of T2 and T3 (identical to each other) and T4 that differs from T2 and T3 by one amino-acid at position 32. The third peak contains the peptide T1 and the fourth peak is composed of a mixture of T1, T2/T3 and T4 (Table 2).

The site of processing has not been precisely determined, but is likely to be located between the aspartate (N) and asparagine (D) residues in the sequence outlined in FIG. 10. Proteases with specific requirements for asparagine residues have been isolated from vacuoles from immature soybean seeds and pumpkin cotyledons (Scott et al., 1992, Hara-Nishimura et al., 1991). This is consistent with the immnunogold localization of the PI in the vacuoles of the papillae and the underlying secretory cells in the stigma of N.alata (Atkinson, 1992). In the case of the N.alata PI, processing analogous to that of peptide hormones is also possible because each of the possible 6 kD peptides are flanked by dibasic residues (Lys-Lys, position-2 & -3 in FIG. 10). However, a system like this has not been described in plants, and it is more likely that the dibasic residues contribute to the predicted hydrophilic loops that present the processing site on the surface of the molecule.

The data from the mass spectrometric analysis shows that once the initial cleavage has occurred the new carboxy terminus is trimmed back (FIG. 10). The EEKKN sequence (SEQ ID NO. 14) is removed completely but the trimming is not precise, sometimes an additional amino acid is removed. Steric hindrance probably prevents further trimming. Occasionally the aspartate is also removed from the N-terminus.

EXAMPLE 3

Production of PI Precursor in Insect Cell (Sf9) Culture Using a Recombinant Baculovirns Vector.

cDNA encoding the PI precursor (FIG. 1) was inserted into the Eco R1 site of the plasmid vector pVL 1392, which is the same as pVL941 (Lucknow and Summers, 1989) except that a multiple cloning site was inserted at the BamH1 site. The plasmid designated pRH11, contains the PI cDNA in the correct orientation with respect to the direction of transcription directed by the polyhedrin promoter. Recombinant baculovirus was obtained by co-transfection of Spodoptera frugiperda cells with baculovirus DNA and pRH11. The recombinant viruses, produced by homologous recombination, were plaque purified and amplified prior to infection of insect cells for protein production. All procedures for production of recombinant baculovirus, titration of the virus and maintenance and infection of the Sf9 cells were obtained from King and Posse (1992). For production of the PI precursor, monolayers of Sf9 cells in large flasks (175 cm²) were infected at the time of confluence with an inoculum of high-titre recombinant virus at a multiplicity of infection of 5–10 pfu/cell. Culture fluid was collected after 4 days of infection, clarified by centrifugation and the PI precursor was purified by application to a Chymotrypsin-Sepharose affinity column as described for the 6 kD PI species from stigmas. PI precursor eluted from the column in 7M urea, pH3 was neutralized immediately with 1M Tris-HCl buffer pH8, dialysed extensively against Milli-Q water, concentrated 20–50 fold by ultrafiltration using a Diaflow YM10 filter and stored frozen at −20° C.

The cDNA clone encoding the PI precursor was engineered into a baculovuirus vector for the production of the precursor from infected insect cells. The insect cells produced a 42 kD protein that cross reacted with the antibodies raised to the 6 kD PI peptides from stigma and bound to the chymotrypsin affinity column. This 42 kD protein was identical in size to the 42 kD precursor produced in the immature stigmas of *N.alata* (FIG. 11) and had the N-terminal sequence LysAlaCysThrLeuAsn (SEQ ID NO. 13) demonstrating that the signal sequence had been processed correctly by the insect cells (FIG. 1). Based on these results, the 42 kD protein produced in the baculovirus expression system will now be referred to as the PI precursor. The 42 kD PI precursor had inhibitory activity against chymotrypsin but no inhibitory activity against trypsin (FIG. 13). Processing of the PI precursor by the endoproteinase AspN led to the production of stable peptides of about 6 kD that were partially purified by reversed phase HPLC (FIG. 12). These peptides have equivalent inhibitory activity against trypsin and chymotrypsin as the 6 kD peptides isolated from stigma, indicating that processing of the precursor is required to activate the trypsin inhibitory activity but not all the chymotrypsin activity. Since AspN cleaves specifically adjacent to Aspartate residues (between Asn-1 and Asp1 in FIG. 10) and has no trimming activity, the peptides produced in vitro will be similiar to those produced in stigmas except for the presence of the sequence EEKKN (SEQ ID NO. 14) at the C-terminus. This provides further evidence that precise processing of the N- and C-termini is not required to obtain an active 6 kD PI peptide. Asp-N1 is more efficient at inhibiting chymotrypsin than trypsin and is thus likely to be predominantly a C1 analogue (FIG. 9b). Asp-N2 is a more efficient trypsin inhibitor and probably contains the T1–T4 analogues.

EXAMPLE 4
Effect of PIs on Protease Activity in Unfractionated Gut Extracts from Various Insects Activity of PIs on gut proteases was measured using the procedure of Christeller et al., (1992) as follows. An aliquot of 1 uM of inhibitor (0–10 µl, at least 5-fold excess over proteases present in the gut) was mixed with 150 µl of 10 mM CAPS buffer, pH 10, and preincubated with each insect gut extract (0–15 µl), for 20 min at 30° C. The reaction was started by the addition of 50 µl of $^{14}$C-labelled casein substrate (400 µg protein, specific activity 25,000–75,000 dpm $mg^{-1}$) and continued for 30 min at 30° C. until 50 µl of cold 30% (w/v) TCA was added to terminate the reaction. After incubation on ice for 30 min, undigested protein was pelleted by centrifugation at 20° C. for 5 min at 10,000 g. The supernatant was removed, mixed with scintillation fluid and the radioactivity measured. Assays were performed at pH 10 except for *L.sericata* and *C.rufifacies* when 10 mM Tris-HCl, pH 8.0 was used.

Table 3 shows the inhibitory activity of the pooled 6 kD PI peptides (C1, T1, T2/T3, T4), the mixture of trypsin inhibitors T2/T3 and T4, and the chymotrypsin inhibitor C1 against the proteases in the gut of various members of the *Lepidoptera, Coleoptera, Orthoptera* and *Diptera*. In most cases, the pooled peptides and the trypsin inhibitors had an equivalent effect against the gut proteases with the degree of inhibition ranging from 37–79% depending on the insect tested. The inhibitors had negligible effect on the gut proteases of the potato tuber moth, *P.opercullela*. The chymotrypsin inhibitor C1 also affected the activity of the proteases but was less effective than the trypsin inhibitors in five cases (*W.cervinata, L.serricata, C.zealandica, P.octo,* sugar cane grub).

The experimental details are described in the legend to FIG. 14. The *N. alata* PI was more effective than Soybean Bowman-Birk inhibitor in reducing cricket weight. It has shown that there is a good correlation between the ability of a proteinase inhibitor to inhibit the enzymes of the insect midgut and its effectiveness in retarding the growth of insects in insect feeding trials (Christeller et al., 1992). FIG. 14 shows that the pooled PIs that inhibited the gut proteases of the black field cricket (*T.commodus*) by 70% in the in vitro assay retarded the growth of the crickets by 30% in a feeding trial conducted over a 10 week period. The correlation between in vitro assays and feeding trials has been confirmed recently by Johnston and collegues (1993) working on growth and development of *Helicoverpa armigera*.

TABLE 2

| HPLC peak | retention time (min) | molecular weight | assigned peptide* |
|---|---|---|---|
| 1 | 15.5 | 5731.5 | C1 |
|   |   | 5644.4 | C1 minus $Ser_{53}$ |
|   |   | 5616.4 | C1 minus $Asp_1$ & $Ser_{53}$ |
|   |   | 55.29.3 | C1 minus $Asp_1$ |
| 2 | 20.5 | 5700.5 | T2/T3 |
|   |   | 5728.5 | T4 |
|   |   | 5585.4 | T2/T3 minus $Asp_1$ |
|   |   | 5613.5 | T4 minus $Asp_1$ |
| 3 | 22.5 | 5725.5 | T1 |
|   |   | 5610.5 | T1 minus $Asp_1$ |
| 4 | 24 | 5654.4 | T1 minus $Ala_{53}$ |
|   |   | 5641.4 | T4 minus $Ser_{53}$ |
|   |   | 5613.4 | T2/T3 minus $Ser_{53}$ |
|   |   | 5539.4 | T1 minus $Asp_1$ & $Ala_{53}$ |
|   |   | 5498.4 | T2/T3 minus $Asp_1$ & $Ser_{53}$ |
|   |   | 5526.4 | T4 minus $Asp_1$ & $Ser_{53}$ |

*See Figure 9 for designation of C1 and T1–T4.

TABLE 3

Effect of *Nicotiana alata* proteinase inhibitors and Potato inhibitor II on casein hydrolysis by crude gut extracts

| | casein hydrolysis (% control) | | |
|---|---|---|---|
| Insect | NaPI | C1 | T2/T3, T4 |
| H. armigera | 33.2 | 32.7 | 30.3 |
| H. punctigera | 26.6 | 29.3 | 28.5 |
| T. commodus | 28.4 | 35.0 | 33.1 |
| A. infusa | 37.5 | 40.2 | 43.3 |
| sugar cane grub | 25.8 | 43.9 | 25.1 |
| W. cervinata | 22.9 | 82.9 | 20.4 |
| E. postvitiana | 39.7 | 45.4 | 41.2 |
| S. litura | 28.1 | 33.6 | 24.8 |
| P. opercullela | 95.8 | 100 | 98.5 |
| C. rufifacies | 29.1 | 37.8 | 28.9 |

TABLE 3-continued

Effect of *Nicotiana alata* proteinase inhibitors and Potato inhibitor II on casein hydrolysis by crude gut extracts

| Insect | casein hydrolysis (% control) | | |
|---|---|---|---|
| | NaPI | C1 | T2/T3, T4 |
| L. serricata | 59.2 | 100 | 63.0 |
| C. zealandica | 31.7 | 54.7 | 32.0 |
| P. octo | 57.1 | 67.2 | 57.4 |
| C. obliquana | 51.1 | 49.1 | 45.5 |
| A. tasmaniae | 28.3 | 34.2 | 39.5 |

Legend to Table 3
NaPI = *N. alata* proteinase inhibitors pooled
C1 = *N. alata* chymotrypsin inhibitor (peaked 1 from HPLC)
T2/T3 = *N. alata* trypsin inhibitors (peak 2 from HPLC)
*Heliothis armigera*, *Helicoverpa armigera*, Tobacco budworm, Lepidoptera
*Heliothis punctigera*, *Helicoverpa punctigera*, Native budworm, Lepidoptera
*Teleogryllus commodus* Black field cricket, Orthoptera
*Agrotis infusa* Common cutworm, adults known as the Bogong moth, Lepidoptera
*Wiseana cervinata* Porina, native to New Zealand, Lepidoptera
*Lucilla sericata* Green blow fly, Diptera, assayed at pH 8
*Chrysomya rufifacies* Hairy maggot blow fly, Diptera, assayed at pH 8
*Aphodius tasmaniae* Tasmanian grass grub = Black-head pasture cockchafer, Coleoptera
*Costelytra zealandica* New Zealand grass grub, Coleoptera
*Spodoptera litura* tropical armyworm, Lepidoptera
*Phthorimaea opercullela* Potato tuber moth, Lepidoptera
*Epiphyas postvittana* Lightbrown apple moth (leafroller), Lepidoptera
*Planotortrix octo* Greenheaded leafroller, Lepidoptera
*Ctenopseustis obliquana* Brownheaded leafroller, Lepidoptera
Sugar cane grub Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

References

Anderson, M. A., McFadden, G. I., Bernatzky, R., Atkinson, A., Orpin, T., Dedman, H., Tregear, G., Fernley, R., Clarke, A. E. (1989) *The Plant Cell* 1: 483–491.

Atkinson, A. H. (1992) PhD thesis, University of Melbourne, Victoria, Australia.

Bernatzky, R., Tanksley, S. D. (1986) *Theor. Appl. Genet.* 72:314–321.

Bradford, M, M. (1976) *Anal. Biochem.* 72:248–254

Brown, W. E., Ryan, C. A. (1984) *Biochemistry* 23:3418–3422.

Bryant, J., Green, T. R., Gurusaddaiah, T., Ryan, C. A. (1976) *Biochemistry* 15:3418–3424.

Cornish, E. C., Pettitt, J. M., Bonig, I., Clarke, A. E. (1987) *Nature* 326: 99–102.

Christeller, J. T., Shaw, B. D., Gardiner, S. E., Dymock, J. (1989) *Insect Biochem.* 19: 2217–231.

Christeller, J. T., Laing, W. A., Markwick, N. P. and Burgess, E. P. J. (1992) *Insect Biochem. Molec. Biol.* 22:735–746

Feinberg, A. P., Vogelstein, B. (1983) *Anal. Biochem.* 132: 6–13.

Graham, J. S., Pearce, G., Merryweather, J., Titani, K., Ericsson, L. H., Ryan, C. A. (1985) *J. Biol. Chem.* 260: 6561–6564.

Graham, J. S., Hall, G., Pearce, G., Ryan, C. A. (1986) *Planta* 169:399–405.

Grego, B., van Driel, I. R., Stearne, P. A., Goding, J. W., Nice, E. G., Simpson, R. J. (1985) *Eur. J. Biochem.* 148:485–491.

Green, T. R., Ryan, C. A. (1972) *Science*: 776–777.

Hara-Nishimura, I., Inoue, K., Nishimura, M. (1991) FEBS Letters 294, 89–93.

Harlow, E., Lane, D. (1988) *Antibodies. A Laboratory Manual*. Cold Spring Harbour Laboratory, New York.

Hass, G. M., Hermodson, M. A., Ryan, C. A., Gentry, L. (1982) *Biochemistry* 21:752–756.

Johnston, K. A., Gatehouse, J. A., Anstee, J. H. (1993) *J. Insect Physiol.* 39, 657–664.

King, L. A. Possee, R. D. (1992). The Baculovirus Expression system. A Laboratory guide. (Chapman & Hall: London, UK).

Kuo, J., Pearce, G. Ryan C. A. (1984) Isolation and characterization of proteinase inhibitor I from etiolated tobacco leaves. *Arch. Biochem. Biophys.* 230: 504–510.

Kyte, J., Doolittle, R. F. (1982) *J. Mol. Biol.* 157: 680–685.

Laemmli, U.K. (1970) *Nature* 227: 680–685.

Lucknow, V. A. and Summers, M. D. (1989). *Virlogy*. 170: 31–39.

Mau, S.-L., Williams, E. G., Atkinson, A., Anderson, M. A., Cornish, E. C., Grego, B., Simpson, R. J., Kheyr-Pour, A., Clarke, A. E. (1986) *Planta* 169:184–191.

Melville, J. C., Ryan, C. A. (1970) *Archives of Biochemistry and Biophysics* 138: 700–702.

Pearce, G., Ryan, C. A., Liljegren, D. (1988) *Planta* 175: 527–531.

Plunkett, G., Senear, D. F., Zuroske, G., Ryan, C. A. (1982) *Arch. Biochem. Biophys.* 213: 463–472.

Richardson, M. (1977) *Phyochemistry* 16:159–169.

Rickauer, M., Fournier, J., Esquerre-Tugaye, M. (1989) *Plant Physiol.* 9:1065–1070.

Ryan, C. A. (1984). Defense responses in plants. In: *Plant Gene Research*, Dennes, E. S., Hohn, B., Hohn, T., King, P., Schell, J., Verma, D. P. S., Eds. New York, Springer-Verlag, 375–386.

Sanchez-Serrano, J. J., Schmidt, R., Schell, J., Willmitzer, L., (1986) *Mol. Gen. Genet.* 203:15–20.

Scott, M. P., Jung, R., Muntz, K., Nielsen, N. C. (1992) *Proc. Natl. Acad. Sci. USA* 89: 658–662.

Thornburg, R. W. An,G., Cleveland, T. E., Johnson, R., Ryan, C. A. (1987). *Proc. Nat. Acad. Sci. USA* 84:744–748.

SEQUENCE LISTING (1) GENERAL INFORMATION:

(iii) NUMBER OF SEQUENCES: 14

(2) INFORMATION FOR SEQ ID NO: 1:

```
    (i) SEQUENCE CHARACTERISTICS:
        (A) LENGTH: 1104 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

AAGGCTTGTA CCTTAAACTG TGATCCAAGA ATTGCCTATG GAGTTTGCCC GCGTTCAGAA      60

GAAAAGAAGA ATGATCGGAT ATGCACCAAC TGTTGCGCAG GCACGAAGGG TTGTAAGTAC     120

TTCAGTGATG ATGGAACTTT TGTTTGTGAA GGAGAGTCTG ATCCTAGAAA TCCAAAGGCT     180

TGTACCTTAA ACTGTGATCC AAGAATTGCC TATGGAGTTT GCCCGCGTTC AGAAGAAAAG     240

AAGAATGATC GGATATGCAC CAACTGTTGC GCAGGCACGA AGGGTTGTAA GTACTTCAGT     300

GATGATGGAA CTTTTGTTTG TGAAGGAGAG TCTGATCCTA GAAATCCAAA GGCTTGTCCT     360

CGGAATTGCG ATCCAAGAAT TGCCTATGGG ATTTGCCCAC TTGCAGAAGA AAAGAAGAAT     420

GATCGGATAT GCACCAACTG TTGCGCAGGC AAAAAGGGTT GTAAGTACTT TAGTGATGAT     480

GGAACTTTTG TTTGTGAAGG AGAGTCTGAT CCTAAAAATC CAAAGGCCTG TCCTCGGAAT     540

TGTGATGGAA GAATTGCCTA TGGGATTTGC CCACTTTCAG AAGAAAAGAA GAATGATCGG     600

ATATGCACCA ACTGCTGCGC AGGCAAAAAG GGTTGTAAGT ACTTTAGTGA TGATGGAACT     660

TTTGTTTGTG AAGGAGAGTC TGATCCTAAA AATCCAAAGG CTTGTCCTCG GAATTGTGAT     720

GGAAGAATTG CCTATGGGAT TGCCCACTT TCAGAAGAAA GAAGAATGA TCGGATATGC       780

ACAAACTGTT GCGCAGGCAA AAAGGGCTGT AAGTACTTTA GTGATGATGG AACTTTTGTT     840

TGTGAAGGAG AGTCTGATCC TAGAAATCCA AAGGCCTGTC CTCGGAATTG TGATGGAAGA     900

ATTGCCTATG GAATTTGCCC ACTTTCAGAA GAAAAGAAGA ATGATCGGAT ATGCACCAAT     960

TGTTGCGCAG GCAAGAAGGG CTGTAAGTAC TTTAGTGATG ATGGAACTTT TATTTGTGAA    1020

GGAGAATCTG AATATGCCAG CAAAGTGGAT GAATATGTTG GTGAAGTGGA GAATGATCTC    1080

CAGAAGTCTA AGGTTGCTGT TTCC                                          1104

(2) INFORMATION FOR SEQ ID NO: 2:

(i) SEQUENCE CHARACTERISTICS:
        (A) LENGTH: 1360 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 97..1200

(xi) SEQUENCE DESCRIPTION: SEQ ID NO: 2:

CGAGTAAGTA TGGCTGTTCA CAGAGTTAGT TTCCTTGCTC TCCTCCTCTT ATTTGGAATG      60

TCTCTGCTTG TAAGCAATGT GGAACATGCA GATGCC AAG GCT TGT ACC TTA AAC       114
                                     Lys Ala Cys Thr Leu Asn
                                      1               5

TGT GAT CCA AGA ATT GCC TAT GGA GTT TGC CCG CGT TCA GAA GAA AAG       162
Cys Asp Pro Arg Ile Ala Tyr Gly Val Cys Pro Arg Ser Glu Glu Lys
             10                  15                  20

AAG AAT GAT CGG ATA TGC ACC AAC TGT TGC GCA GGC ACG AAG GGT TGT       210
Lys Asn Asp Arg Ile Cys Thr Asn Cys Cys Ala Gly Thr Lys Gly Cys
         25                  30                  35
```

-continued

```
AAG TAC TTC AGT GAT GAT GGA ACT TTT GTT TGT GAA GGA GAG TCT GAT       258
Lys Tyr Phe Ser Asp Asp Gly Thr Phe Val Cys Glu Gly Glu Ser Asp
 40                  45                  50

CCT AGA AAT CCA AAG GCT TGT ACC TTA AAC TGT GAT CCA AGA ATT GCC       306
Pro Arg Asn Pro Lys Ala Cys Thr Leu Asn Cys Asp Pro Arg Ile Ala
 55                  60                  65                  70

TAT GGA GTT TGC CCG CGT TCA GAA GAA AAG AAG AAT GAT CGG ATA TGC       354
Tyr Gly Val Cys Pro Arg Ser Glu Glu Lys Lys Asn Asp Arg Ile Cys
                     75                  80                  85

ACC AAC TGT TGC GCA GGC ACG AAG GGT TGT AAG TAC TTC AGT GAT GAT       402
Thr Asn Cys Cys Ala Gly Thr Lys Gly Cys Lys Tyr Phe Ser Asp Asp
                 90                  95                 100

GGA ACT TTT GTT TGT GAA GGA GAG TCT GAT CCT AGA AAT CCA AAG GCT       450
Gly Thr Phe Val Cys Glu Gly Glu Ser Asp Pro Arg Asn Pro Lys Ala
             105                 110                 115

TGT CCT CGG AAT TGC GAT CCA AGA ATT GCC TAT GGG ATT TGC CCA CTT       498
Cys Pro Arg Asn Cys Asp Pro Arg Ile Ala Tyr Gly Ile Cys Pro Leu
         120                 125                 130

GCA GAA GAA AAG AAG AAT GAT CGG ATA TGC ACC AAC TGT TGC GCA GGC       546
Ala Glu Glu Lys Lys Asn Asp Arg Ile Cys Thr Asn Cys Cys Ala Gly
135                 140                 145                 150

AAA AAG GGT TGT AAG TAC TTT AGT GAT GAT GGA ACT TTT GTT TGT GAA       594
Lys Lys Gly Cys Lys Tyr Phe Ser Asp Asp Gly Thr Phe Val Cys Glu
                155                 160                 165

GGA GAG TCT GAT CCT AAA AAT CCA AAG GCC TGT CCT CGG AAT TGT GAT       642
Gly Glu Ser Asp Pro Lys Asn Pro Lys Ala Cys Pro Arg Asn Cys Asp
            170                 175                 180

GGA AGA ATT GCC TAT GGG ATT TGC CCA CTT TCA GAA GAA AAG AAG AAT       690
Gly Arg Ile Ala Tyr Gly Ile Cys Pro Leu Ser Glu Glu Lys Lys Asn
        185                 190                 195

GAT CGG ATA TGC ACC AAC TGC TGC GCA GGC AAA AAG GGT TGT AAG TAC       738
Asp Arg Ile Cys Thr Asn Cys Cys Ala Gly Lys Lys Gly Cys Lys Tyr
    200                 205                 210

TTT AGT GAT GAT GGA ACT TTT GTT TGT GAA GGA GAG TCT GAT CCT AAA       786
Phe Ser Asp Asp Gly Thr Phe Val Cys Glu Gly Glu Ser Asp Pro Lys
215                 220                 225                 230

AAT CCA AAG GCT TGT CCT CGG AAT TGT GAT GGA AGA ATT GCC TAT GGG       834
Asn Pro Lys Ala Cys Pro Arg Asn Cys Asp Gly Arg Ile Ala Tyr Gly
                235                 240                 245

ATT TGC CCA CTT TCA GAA GAA AAG AAG AAT GAT CGG ATA TGC ACA AAC       882
Ile Cys Pro Leu Ser Glu Glu Lys Lys Asn Asp Arg Ile Cys Thr Asn
            250                 255                 260

TGT TGC GCA GGC AAA AAG GGC TGT AAG TAC TTT AGT GAT GAT GGA ACT       930
Cys Cys Ala Gly Lys Lys Gly Cys Lys Tyr Phe Ser Asp Asp Gly Thr
        265                 270                 275

TTT GTT TGT GAA GGA GAG TCT GAT CCT AGA AAT CCA AAG GCC TGT CCT       978
Phe Val Cys Glu Gly Glu Ser Asp Pro Arg Asn Pro Lys Ala Cys Pro
    280                 285                 290

CGG AAT TGT GAT GGA AGA ATT GCC TAT GGA ATT TGC CCA CTT TCA GAA      1026
Arg Asn Cys Asp Gly Arg Ile Ala Tyr Gly Ile Cys Pro Leu Ser Glu
295                 300                 305                 310

GAA AAG AAG AAT GAT CGG ATA TGC ACC AAT TGT TGC GCA GGC AAG AAG      1074
Glu Lys Lys Asn Asp Arg Ile Cys Thr Asn Cys Cys Ala Gly Lys Lys
                315                 320                 325

GGC TGT AAG TAC TTT AGT GAT GAT GGA ACT TTT ATT TGT GAA GGA GAA      1122
Gly Cys Lys Tyr Phe Ser Asp Asp Gly Thr Phe Ile Cys Glu Gly Glu
            330                 335                 340

TCT GAA TAT GCC AGC AAA GTG GAT GAA TAT GTT GGT GAA GTG GAG AAT      1170
Ser Glu Tyr Ala Ser Lys Val Asp Glu Tyr Val Gly Glu Val Glu Asn
```

-continued

```
              345                 350                 355
GAT CTC CAG AAG TCT AAG GTT GCT GTT TCC TAAGTCCTAA CTAATAATAT            1220
Asp Leu Gln Lys Ser Lys Val Ala Val Ser
        360                 365

GTAGTCTATG TATGAAACAA AGGCATGCCA ATATGCTCTG TCTTGCCTGT AATCTGTAAT        1280

ATGGTAGTGG AGCTTTTCCA CTGCCTGTTT AATAAGAAAT GGAGCACTAG TTTGTTTTAG        1340

TTAAAAAAAA AAAAAAAAA                                                    1360
```

(2) INFORMATION FOR SEQ ID NO: 3:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO: 3:

```
Lys Ala Cys Thr Leu Asn Cys Asp Pro Arg Ile Ala Tyr Gly Val Cys
 1               5                  10                  15

Pro Arg Ser Glu Glu Lys Lys Asn Asp Arg Ile Cys Thr Asn Cys Cys
            20                  25                  30

Ala Gly Thr Lys Gly Cys Lys Tyr Phe Ser Asp Asp Gly Thr Phe Val
        35                  40                  45

Cys Glu Gly Glu Ser Asp Pro Arg Asn Pro Lys Ala Cys Thr Leu Asn
    50                  55                  60

Cys Asp Pro Arg Ile Ala Tyr Gly Val Cys Pro Arg Ser Glu Glu Lys
65                  70                  75                  80

Lys Asn Asp Arg Ile Cys Thr Asn Cys Cys Ala Gly Thr Lys Gly Cys
                85                  90                  95

Lys Tyr Phe Ser Asp Asp Gly Thr Phe Val Cys Glu Gly Glu Ser Asp
            100                 105                 110

Pro Arg Asn Pro Lys Ala Cys Pro Arg Asn Cys Asp Pro Arg Ile Ala
        115                 120                 125

Tyr Gly Ile Cys Pro Leu Ala Glu Glu Lys Lys Asn Asp Arg Ile Cys
    130                 135                 140

Thr Asn Cys Cys Ala Gly Lys Lys Gly Cys Lys Tyr Phe Ser Asp Asp
145                 150                 155                 160

Gly Thr Phe Val Cys Glu Gly Glu Ser Asp Pro Lys Asn Pro Lys Ala
                165                 170                 175

Cys Pro Arg Asn Cys Asp Gly Arg Ile Ala Tyr Gly Ile Cys Pro Leu
            180                 185                 190

Ser Glu Glu Lys Lys Asn Asp Arg Ile Cys Thr Asn Cys Cys Ala Gly
        195                 200                 205

Lys Lys Gly Cys Lys Tyr Phe Ser Asp Asp Gly Thr Phe Val Cys Glu
    210                 215                 220

Gly Glu Ser Asp Pro Lys Asn Pro Lys Ala Cys Pro Arg Asn Cys Asp
225                 230                 235                 240

Gly Arg Ile Ala Tyr Gly Ile Cys Pro Leu Ser Glu Glu Lys Lys Asn
                245                 250                 255

Asp Arg Ile Cys Thr Asn Cys Cys Ala Gly Lys Lys Gly Cys Lys Tyr
            260                 265                 270

Phe Ser Asp Asp Gly Thr Phe Val Cys Glu Gly Glu Ser Asp Pro Arg
        275                 280                 285

Asn Pro Lys Ala Cys Pro Arg Asn Cys Asp Gly Arg Ile Ala Tyr Gly
```

-continued

```
                  290                 295                 300
Ile Cys Pro Leu Ser Glu Glu Lys Lys Asn Asp Arg Ile Cys Thr Asn
305                 310                 315                 320

Cys Cys Ala Gly Lys Lys Gly Cys Lys Tyr Phe Ser Asp Asp Gly Thr
                325                 330                 335

Phe Ile Cys Glu Gly Glu Ser Glu Tyr Ala Ser Lys Val Asp Glu Tyr
                340                 345                 350

Val Gly Glu Val Glu Asn Asp Leu Gln Lys Ser Lys Val Ala Val Ser
                355                 360                 365

(2) INFORMATION FOR SEQ ID NO: 4:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 4:

Lys Ala Cys Thr Leu Asn Cys Asp Pro Arg Ile Ala Tyr Gly Val Cys
1               5                  10                  15

Pro Arg Ser Glu Glu Lys Lys Asn
                20

(2) INFORMATION FOR SEQ ID NO: 5:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 5:

Asp Arg Ile Cys Thr Asn Cys Cys Ala Gly Thr Lys Gly Cys Lys Tyr
1               5                  10                  15

Phe Ser Asp Asp Gly Thr Phe Val Cys Glu Gly Glu Ser Asp Pro Arg
                20                  25                  30

Asn Pro Lys Ala Cys Thr Leu Asn Cys Asp Pro Arg Ile Ala Tyr Gly
                35                  40                  45

Val Cys Pro Arg Ser Glu Glu Lys Lys Asn
                50                  55

(2) INFORMATION FOR SEQ ID NO: 6:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 6:

Asp Arg Ile Cys Thr Asn Cys Cys Ala Gly Thr Lys Gly Cys Lys Tyr
1               5                  10                  15

Phe Ser Asp Asp Gly Thr Phe Val Cys Glu Gly Glu Ser Asp Pro Arg
                20                  25                  30

Asn Pro Lys Ala Cys Pro Arg Asn Cys Asp Pro Arg Ile Ala Tyr Gly
                35                  40                  45
```

```
Ile Cys Pro Leu Ala Glu Glu Lys Lys Asn
    50                  55
```

(2) INFORMATION FOR SEQ ID NO: 7:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 7:

```
Asp Arg Ile Cys Thr Asn Cys Cys Ala Gly Lys Lys Gly Cys Lys Tyr
1               5                   10                  15

Phe Ser Asp Asp Gly Thr Phe Val Cys Glu Gly Glu Ser Asp Pro Lys
            20                  25                  30

Asn Pro Lys Ala Cys Pro Arg Asn Cys Asp Gly Arg Ile Ala Tyr Gly
            35                  40                  45

Ile Cys Pro Leu Ser Glu Glu Lys Lys Asn
    50                  55
```

(2) INFORMATION FOR SEQ ID NO: 8:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 8:

```
Asp Arg Ile Cys Thr Asn Cys Cys Ala Gly Lys Lys Gly Cys Lys Tyr
1               5                   10                  15

Phe Ser Asp Asp Gly Thr Phe Val Cys Glu Gly Glu Ser Asp Pro Lys
            20                  25                  30

Asn Pro Lys Ala Cys Pro Arg Asn Cys Asp Gly Arg Ile Ala Tyr Gly
            35                  40                  45

Ile Cys Pro Leu Ser Glu Glu Lys Lys Asn
    50                  55
```

(2) INFORMATION FOR SEQ ID NO: 9:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 9:

```
Asp Arg Ile Cys Thr Asn Cys Cys Ala Gly Lys Lys Gly Cys Lys Tyr
1               5                   10                  15

Phe Ser Asp Asp Gly Thr Phe Val Cys Glu Gly Glu Ser Asp Pro Arg
            20                  25                  30

Asn Pro Lys Ala Cys Pro Arg Asn Cys Pro Gly Arg Ile Ala Tyr Gly
            35                  40                  45

Ile Cys Pro Leu Ser Glu Glu Lys Lys Asn
    50                  55
```

(2) INFORMATION FOR SEQ ID NO: 10:

(i) SEQUENCE CHARACTERISTICS:
       (A) LENGTH: 54 amino acids
       (B) TYPE: amino acid
       (C) STRANDEDNESS: <Unknown>
       (D) TOPOLOGY: linear (ii) MOLECULE TYPE: protein (xi) SEQUENCE DESCRIPTION: SEQ ID NO: 10:

Asp Arg Ile Cys Thr Asn Cys Cys Ala Gly Lys Lys Gly Cys Lys Tyr
1               5                   10                  15

Phe Ser Asp Asp Gly Thr Phe Ile Cys Glu Gly Glu Ser Glu Thr Ala
            20                  25                  30

Ser Lys Val Asp Glu Tyr Val Gly Glu Val Glu Asn Asp Leu Gln Lys
        35                  40                  45

Ser Lys Val Ala Val Ser
        50

(2) INFORMATION FOR SEQ ID NO: 11:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 11:

Asp Arg Ile Cys Thr Asn Cys Cys Ala Gly Thr Lys Gly
1               5                   10

(2) INFORMATION FOR SEQ ID NO: 12:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 12:

Asp Arg Ile Cys Thr Asn Cys Cys Ala Gly Lys Lys Gly
1               5                   10

(2) INFORMATION FOR SEQ ID NO: 13:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 13:

Lys Ala Cys Thr Leu Asn
1               5

(2) INFORMATION FOR SEQ ID NO: 14:

(i) SEQUENCE CHARACTERISTICS:
       (A) LENGTH: 5 amino acids
       (B) TYPE: amino acid -continued

```
        (C) STRANDEDNESS: single
        (D) TOPOLOGY: linear (ii) MOLECULE TYPE: peptide (xi) SEQUENCE DESCRIPTION: SEQ ID NO: 14:

Glu Glu Lys Lys Asn
1               5
```

What is claimed is:

1. A genetic construct comprising a nucleotide sequence which encodes or is complementary to a sequence which encodes a type II serine proteinase inhibitor (PI) precursor from a plant of the genus *Nicotiana* or monomer of said PI precursor, wherein said precursor comprises the amino acid sequence as set forth in SEQ ID NO: 3, and said precursor comprises at least three PI monomers and wherein at least one of said monomers has a chymotrypsin specific site and at least one other of said monomers has a trypsin specific site, and wherein said genetic construct further comprises (1) expression means to permit expression of said nucleotide sequence, (2) replication means to permit replication in a plant cell, or (3) integration means to permit stable integration of said nucleotide sequence into a plant cell genome.

2. A transgenic plant carrying a genetic construct, said genetic construct comprising a nucleotide sequence which encodes or is complementary to a sequence which encodes a type II serine proteinase inhibitor (PI) precursor from a plant of the genus *Nicotiana* or monomer of said PI precursor, wherein said precursor comprises at least three PI monomers and wherein at least one of said monomers has a chymotrypsin specific site and at least one other of said monomers has a trypsin specific site, and wherein said precursor comprises the amino acid sequence as set forth in SEQ ID NO: 3.

3. A genetic construct comprising a nucleotide sequence which encodes or is complementary to a sequence which encodes a type II serine proteinase inhibitor (PI) precursor from a plant of the genus *Nicotiana* or monomer of said PI precursor, wherein said nucleotide sequence comprises SEQ ID NO: 1, wherein said precursor comprises at least three PI monomers and wherein at least one of said monomers has a chymotrypsin specific site and at least one of said other monomers has a trypsin specific site, and wherein said genetic construct further comprises (1) expression means to permit expression of said nucleotide sequence, (2) replication means to permit replication in a plant cell, or (3) integration means to permit stable integration of said nucleotide sequence into a plant cell genome.

4. The genetic construct according to claim 1 or 3, wherein said nucleotide sequence encodes a peptide which comprises a sequence as set forth in any one of SEQ ID NOS: 4–10.

5. A transgenic plant carrying a genetic construct, said genetic construct comprising a nucleotide sequence which encodes or is complementary to a sequence which encodes a type II serine proteinase inhibitor (PI) precursor from a plant of the genus *Nicotiana* or monomer of said PI precursor, wherein said nucleotide sequence comprises SEQ ID NO: 1, wherein said precursor comprises at least three PI monomers and wherein at least one of said monomers has a chymotrypsin specific site and at least one of said other monomers has a trypsin specific site.

6. A genetic construct comprising a nucleotide sequence which encodes or is complementary to a sequence which encodes a type II serine proteinase inhibitor (PI) precursor from a plant or monomer of said PI precursor, wherein said nucleotide sequence hybridizes to the complement sequence of SEQ ID NO: 1 under conditions which comprise (1) hybridization at 68° C., and washing at 68° C. in 2×SSC, 0.1% w/v SDS or in 0.2×SSC, 1% w/v SDS, or (2) hybridization at 40° C. in 50% v/v formamide, and washing sequentially in 4×SSC at room temperature, 2×SSC at room temperature and 1×SSC at 40° C., wherein said precursor comprises at least three PI monomers and wherein at least one of said monomers has a chymotrypsin specific site and at least one other of said monomers has a trypsin specific site, and wherein said genetic construct further comprises (1) expression means to permit expression of said nucleotide sequence, (2) replication means to permit replication in a plant cell, or (3) integration means to permit stable integration of said nucleotide sequence into a plant cell genome.

7. A transgenic plant comprising the genetic construct of claim 6.

8. The transgenic plant according to claim 2 or 5 wherein said transgenic plant produces one or more PI monomers selected from the list consisting of SEQ ID NO: 5, SEQ ID NO: 6, SEQ ID NO: 7, SEQ ID NO: 8 and SEQ ID NO: 9.

9. The transgenic plant according to claim 2 or 5 wherein said transgenic plant produces a peptide consisting of SEQ ID NO: 4 or SEQ ID NO: 10.

* * * * *